(12) United States Patent
Boeke et al.

(10) Patent No.: US 10,047,366 B2
(45) Date of Patent: Aug. 14, 2018

(54) TELOMERATOR-A TOOL FOR CHROMOSOME ENGINEERING

(71) Applicant: THE JOHNS HOPKINS UNIVERSITY, Baltimore, MD (US)

(72) Inventors: Jef D. Boeke, Baltimore, MD (US); Leslie Mitchell, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/772,832

(22) PCT Filed: Mar. 6, 2014

(86) PCT No.: PCT/US2014/021158
§ 371 (c)(1),
(2) Date: Sep. 4, 2015

(87) PCT Pub. No.: WO2014/138379
PCT Pub. Date: Sep. 12, 2014

(65) Prior Publication Data
US 2016/0017344 A1    Jan. 21, 2016

Related U.S. Application Data

(60) Provisional application No. 61/773,206, filed on Mar. 6, 2013.

(51) Int. Cl.
*C12N 15/65* (2006.01)
*C12N 15/81* (2006.01)
*C12N 15/90* (2006.01)

(52) U.S. Cl.
CPC ............ *C12N 15/81* (2013.01); *C12N 15/65* (2013.01); *C12N 15/905* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 1,329,559 A | 2/1920 | Tesla | |
| 5,990,390 A * | 11/1999 | Lundquist | C07K 14/325 536/23.71 |
| 6,183,969 B1 | 2/2001 | Gabriel | |
| 2003/0113887 A1 | 6/2003 | Dujon et al. | |
| 2006/0288665 A1 | 12/2006 | Imao | |
| 2008/0160616 A1 | 7/2008 | Dujon et al. | |

FOREIGN PATENT DOCUMENTS

WO    2000-06715 A1    2/2000

OTHER PUBLICATIONS

Nosek, J., et al., "On the origin of telomeres: a glimpse at the pre-telomerase world", Bioessays, (2006), vol. 28, pp. 182-190.
Woods, J., et al., "Autonomous replication of foreign DNA in histoplosma capsulatum; role of native telomeric sequences", Journal of Bacteriology, (Feb. 1993), vol. 175, No. 3, pp. 636-641.
Douville, N., et al., "DNA linearization through confinement in nanofluidic channels", Analytical and Bioanalytical Chemistry (2008) vol. 391, pp. 2395-2409.
Ryan, D. et al., 2013. "Single-layer domino diodes via optofluidic lithography for ultra-low reynolds number applications". Proceedings of 26th IEEE Micro Electro Mechanical Systems Conference, pp. 153-156.
Thompson, S., et al. 2011. "Investigation of a flat-plate oscillating heat pipe with teslatype check valves". Experimental Thermal and Fluid Science, 35(7), pp. 1265-1273.
Forster, F. K., et al. 1995. "Design, fabrication and testing of fixed-valve micro-pumps". Proceedings of the ASME Fluids Engineering Division. FED-vol. 234: 39-44.
Morganti, E., et al. 2005. "Microfluidics for the treatment of the hydrocephalus". In Proceedings of International Conference on Sensing Technology, Palmerston North.
Stemme, E., et al. 1993. "A valveless diffuser/nozzle-based fluid pump". Sensors and Actuators A: Physical, 39(2), pp. 159-167.
Andersson, H., et al. 2001. "A valve-less diffuser micropump for microfluidic analytical systems". Sensors and Actuators B: Chemical, 72(3), pp. 259-265.
Olsson, A., et al. 1997. "Micromachined flat-walled valveless diffuser pumps". Microelectromechanical Systems, Journal of, 6(2), pp. 161-166.
Bardell, R. L., 2000. "The diodicity mechanism of tesla-type no-moving-parts valves". PhD thesis, University of Washington, Seattle, WA, USA.
Gamboa, A. R., et al. 2005. "Improvements in fixed-valve micropump performance through shape optimization of valves". Journal of Fluids Engineering, 127(2), 3, pp. 339-347.
Pingen, G., 2008. "Optimal design for fluidic systems: Topology and shape optimization with the lattice boltzmann method". PhD thesis, University of Colorado, Boulder, Colorado, USA.
Pingen, G., et al. 2008. "A parallel schur complement solver for the solution of the adjoint steady-state lattice boltzmann equations: application to design optimisation". International Journal of Computational Fluid Dynamics, 22(7), pp. 457-464.
Clabuk, H., et al. 1992. "Optimum plane diffusers in laminar flow". Journal of Fluid Mechanics, 237, 3, pp. 373-393.
Liu, Z., et al. 2012. "Optimization of micro venturi diode in steady flow at low reynolds number". Engineering Optimization, 44(11), pp. 1389-1404.
Borrvall, T., et al. 2003. "Topology optimization of fluids in stokes flow". International Journal for Numerical Methods in Fluids, 41(1), pp. 77-107.

(Continued)

*Primary Examiner* — James S Ketter
(74) *Attorney, Agent, or Firm* — Johns Hopkins Technology Ventures

(57) ABSTRACT

The present invention relates to the field of chromosome engineering. More specifically, the present invention provides methods and compositions useful for inducibly linearizing circular DNA molecules in vivo in yeast. In one embodiment, a comprises a nucleic acid encoding a selectable marker, wherein the nucleic acid encoding a selectable marker comprises an intron comprising an endonuclease recognition site flanked by telomere seed sequences.

36 Claims, 7 Drawing Sheets

(56) References Cited

OTHER PUBLICATIONS

Guest. J. K., 2009. "Topology optimization with multiple phase projection". Computer Methods in Applied Mechanics and Engineering, 199(14), pp. 123-135.
A. Goffeau, et al., "Life with 6000 Genes". Science 274, 546 (Oct. 25, 1996).
L. Clarke, et al. "Isolation of a yeast centromere and construction of functional small circular chromosomes." Nature 287, 504 (Oct. 9, 1980).
J. Shampay, et al. "DNA Sequences of telomeres maintained in yeast." Nature 310, 154 (Jul. 12-18, 1984).
R. W. Walmsley, et al. "Unusual DNA sequences Associated with the ends of yeast chromosomes." Nature 310, 157 (Jul. 12-18, 1984).
Y. Ueda, et al., "Large-scale genome reorganization in *Saccharomyces cerevisiae* through combinatorial loss of mini-chromosomes." J Biosci Bioeng 113, 675 (Jun. 2012).
K. Murakami et al., "Large scale deletions in the *Saccharomyces cerevisiae* genome create strains with altered regulation of carbon metabolism". Appl Microbial Biotechnol 75, 589 (Jun. 2007).
R. J. Reid, et al. "Chromosome-Scale Genetic Mapping Using a Set of 16 Conditionally Stable *Saccharomyces cerevisiae* Chromosomes". Genetics 180, 1799 (Dec. 2008).
Dymond, J. S. et al. "Synthetic chromosome arms function in yeast and generate phenotypic diversity by design". (2011). Nature 477, 471-476.
Plessis, A., et al. "Site-specific recombination determined by I-SceI, a mitochondrial group I intron-encoded endonuclease expressed in the yeast nucleus". Genetics 130, 451-460 (1992).
Colleaux, L., et al. "Recognition and cleavage site of the intron-encoded omega transposase". Proc Natl Acad Sci USA 85, 6022-6026 (1988).
Davis, A. P., et al. "RAD51-dependent break-induced replication in yeast". Mol Cell Biol 24, 2344-2351 (2004).
Yu, X. & Gabriel, A. "Patching broken chromosomes with extranuclear cellular DNA". Mol Cell 4, 873-881, doi: S1097-2765(00)80397-4 [pii] (1999).
Boeke, D., et al. "5-Fluoroorotic acid as a selective agent in yeast molecular genetics". Methods Enzymol 154, 164-175, doi:0076-6879(87)54076-9 [pii] (1987).
Sikorski, R. S. et al. "System of shuttle vectors and yeast host strains designed for efficient manipulation of DNA in *Saccharomyces cerevisiae*". Genetics 122, 19-27 (1989).
Brachmann, C. B. et al. "Designer deletion strains derived from *Saccharomyces cerevisiae* S288C: a useful set of strains and plasmids for PCR-mediated gene disruption and other applications". (1998) Yeast 14, 115-132.
Surosky, R. T., et al. "The mitotic stability of deletion derivatives of chromosome III in yeast". Proc Natl Acad Sci U S A 83, 414-418 (1986).
W. J. Blake, et al., "Pairwise selection assembly for sequence-independent construction of long-length DNA". Nucleic Acids Res 38, 2594 (May 2010).
O. M. Aparicio, et al. "Modifiers of Position Effect Are Shared between Telomeric and Silent Mating-Type Loci in *S. cerevisiae*". Cell 66, 1279 (Sep. 20, 1991).
S. Imai, et al. "Transcriptional silencing and longevity protein Sir2 is an NAD-dependent histone deacetylase". Nature 403, 795 (Feb. 17, 2000).
G. M. Dani, et al. "Mitotic and meiotic stability of linear plasmids in yeast". Proc. Natl Acad Sci US A 80, 3406 (Jun. 1983).
A. W. Murray, et al. "Construction of Artificial Chromosomes in Yeast". Nature 305, 189 (Sep. 15-21, 1983).
J.E. Haber, et al. "Meiotic and Mitotic Behavior of Dicentric Chromosomes in *Saccharomyces cerevisiae*". Genetics 106, 185 (Feb. 1984).
A. W. Murray, et al. "Construction and Behavior of Circularly Permuted and Telocentric Chromosomes in *Saccharomyces cerevisiae*". Mol Cell Biol 6, 3166 (Sep. 1986).
Y. Kazuki, et al., "Refined human artificial chromosome vectors for gene therapy and animal transgenesis". Gene Ther 18, 384 (Apr. 2011).
R. Saffery, et al., "Construction of neocentromere-based human minichromosomes by telomere-associated chromosomal truncation". Proc Natl Acad Sci US A 98, 5705 (May 8, 2001).
J. J. Harrington, et al. "Formation of de novo centromeres and construction of first-generation human artificial microchromosomes". Nat Genet 15, 345 (Apr. 1997).
T. A. Ebersole, et al., "Construction of neocentromere-based human minichromosomes by telomere-associated chromosomal truncation". Hum Mol Genet 9, 1623 (Jul. 1, 2000).
M. Ikeno, et al., "Construction of YAC-Based mammalian artificial chromosomes". Nat Biotechnol 16, 431 (May 1998).
D. Moralli, et al. "Insertion of a lox P site in a size-reduced human accessory chromosome". Cytogenet Cell Genet 94, 113 (2001 ).
Y. Iida, et al., "Human Artificial Chromosome with a Conditional Centromere for Gene Delivery and Gene Expression". DNA Res 17, 293 (Oct. 2010).
A. J. Noel, et al. "DNA Recognition by the Homing Endonuclease PI-SceI Involves a Divalent Metal Ion Cofactor-induced Conformational Change." J Biol Chem 279, 6794 (Feb. 20, 2004).
D. G. Gibson, et al., "Enzymatic assembly of DNA molecules up to several hundred kilobases". Nat Methods 6, 343 (May 2009).
M. Lisby, et al. "Colocalization of multiple DNA double-strand breaks at a single Rad52 repair centre". Nat. Cell Biol 5, 572 (Jun. 2003).
D. C. Schwartz, et al. "Separation of Yeast Chromosome-Sized DNAs by Pulsed Field Gradient Gel Electrophoresis". Cell 37, 67 (May 1984).
E. A. Winzeler, et al., "Functional Characterization of the *S. cerevisiae* Genome by Gene Deletion and Parallel Analysis". Science 285, 901 (Aug. 6, 1999).

* cited by examiner

SEQUENCE LISTING

<160> NUMBER OF SEQ ID NOS: 13

<210> SEQ ID NO 1
<211> LENGTH: 41
<212> TYPE: DNA
<213> ORGANISM: Saccharomyces cerevisiae

<400> SEQUENCE: 1
tgtgtggtgt gtgggtgtgt gtgggtgtgt gggtgtgtgg g          41

<210> SEQ ID NO 2
<211> LENGTH: 18
<212> TYPE: DNA
<213> ORGANISM: Artificial Sequence
<220> FEATURE:
<223> OTHER INFORMATION: I-SceI recognition sequence

<400> SEQUENCE: 2
tagggataac agggtaat                                    18

<210> SEQ ID NO 3
<211> LENGTH: 40
<212> TYPE: DNA
<213> ORGANISM: Saccharomyces cerevisiae

<400> SEQUENCE: 3
cacccaccac acacacccac acacaccaca cacccaccca           40

<210> SEQ ID NO 4
<211> LENGTH: 99
<212> TYPE: DNA
<213> ORGANISM: Artificial Sequence
<220> FEATURE:
<223> OTHER INFORMATION: TeSS-ISceI-TesSS sequence

<400> SEQUENCE: 4
tgtgtggtgt gtgggtgtgt gtgggtgtgt gggtgtgtgg gtagggataa cagggtaatc    60
acccaccaca cacccaca cacaccacac acccaccca                99

<210> SEQ ID NO 5
<211> LENGTH: 27
<212> TYPE: DNA
<213> ORGANISM: Artificial Sequence

```
<220> FEATURE:
<223> OTHER INFORMATION: Forward primer

<400> SEQUENCE: 5
atcccattta actgtaagaa gaattgc                                              27

<210> SEQ ID NO 6
<211> LENGTH: 27
<212> TYPE: DNA
<213> ORGANISM: Artificial Sequence
<220> FEATURE:
<223> OTHER INFORMATION: Reverse primer

<400> SEQUENCE: 6
ggagagtgaa aaatagtaaa aaaaggt                                              27

<210> SEQ ID NO 7
<211> LENGTH: 20
<212> TYPE: DNA
<213> ORGANISM: Artificial Sequence
<220> FEATURE:
<223> OTHER INFORMATION: Primer upstream of URA3 promoter.

<400> SEQUENCE: 7
cccgggggat ccggtgattg                                                      20

<210> SEQ ID NO 8
<211> LENGTH: 20
<212> TYPE: DNA
<213> ORGANISM: Artificial Sequence
<220> FEATURE:
<223> OTHER INFORMATION: Primer downstream of URA3 terminator

<400> SEQUENCE: 8
ccaaagctgg agctccaccg                                                      20

<210> SEQ ID NO 9
<211> LENGTH: 903
<212> TYPE: DNA
<213> ORGANISM: Artificial Sequence
<220> FEATURE:
<223> OTHER INFORMATION: URA3 coding sequence with TeSS-ISceI-Tess
      sequence inserted after the start codon

<400> SEQUENCE: 9
atgtgtgtgg tgtgtgggtg tgtgtgggtg tgtgggtgtg tgggtaggga taacagggta          60
atcacccacc acacacaccc acacacacca cacacccacc catcgaaagc tacatataag         120
gaacgtgctg ctactcatcc tagtcctgtt gctgccaagc tatttaatat catgcacgaa         180
aagcaaacaa acttgtgtgc ttcattggat gttcgtacca ccaaggaatt actggagtta         240
gttgaagcat taggtcccaa aatttgttta ctaaaaacac atgtggatat cttgactgat         300
ttttccatgg agggcacagt taagccgcta aaggcattat ccgccaagta cattttttta        360
ctcttcgaag acagaaaatt tgctgacatt ggtaatacag tcaaattgca gtactctgcg         420
ggtgtataca gaatagcaga atgggcagac attacgaatg cacacggtgt ggtgggccca         480
ggtattgtta gcggtttgaa gcaggcggca gaagaagtaa caaaggaacc tagaggcctt         540
ttgatgttag cagaattgtc atgcaagggc tccctatcta ctggagaata tactaagggt         600
actgttgaca ttgcgaagag cgacaaagat tttgttatcg gctttattgc tcaaagagac         660
atgggtggaa gagatgaagg ttacgattgg ttgattatga cacccggtgt gggtttagat         720
gacaagggag atgcattggg tcaacagtat agaaccgtgg atgatgtggt gtctacagga         780
```

```
tctgacatta ttattgttgg aagaggacta tttgcaaagg gaagggatgc taaggtagag     840
ggtgaacgtt acagaaaagc aggctgggaa gcatatttga agatgcggg ccagcaaaac     900 taa                                                                  903
```

<210> SEQ ID NO 10
<211> LENGTH: 921
<212> TYPE: DNA
<213> ORGANISM: Artificial Sequence
<220> FEATURE:
<223> OTHER INFORMATION: Clone 1

<400> SEQUENCE: 10

```
atgtgtgtgg tgtgtgggtg tgtgtgggtg tgtgggtgtg tgtgggtgtg tgggtgtgtg     60
ggtagggata acagggtaat cacccaccac acacacccac acacaccaca cacccaccca    120
tcgaaagcta catataagga acgtgctgct actcatccta gtcctgttgc tgccaagcta    180
tttaatatca tgcacgaaaa gcaaacaaac ttgtgtgctt cattggatgt tcgtaccacc    240
aaggaattac tggagttagt tgaagcatta ggtcccaaaa tttgtttact aaaaacacat    300
gtggatatct tgactgattt ttccatggag gcacagtta agccgctaaa ggcattatcc     360
gccaagtaca atttttact cttcgaagac agaaaatttg ctgacattgg taatacagtc    420
aaattgcagt actctgcggg tgtatacaga atagcagaat gggcagacat tacgaatgca    480
cacggtgtgg tgggcccagg tattgttagc ggtttgaagc aggcggcaga agaagtaaca    540
aaggaaccta gaggcctttt gatgttagca gaattgtcat gcaagggctc cctatctact    600
ggagaatata ctaagggtac tgttgacatt gcgaagagcg acaaagattt tgttatcggc    660
tttattgctc aaagagacat gggtggaaga atgaaggtt acgattggtt gattatgaca    720
cccggtgtgg gtttagatga caagggagac gcattgggtc aacagtatag aaccgtggat    780
gatgtggtct ctacaggatc tgacattatt attgttggaa gaggactatt tgcaaaggga    840
agggatgcta agtagaggg tgaacgttac agaaaagcag gctgggaagc atatttgaga    900
agatgcggcc agcaaaacta a                                              921
```

<210> SEQ ID NO 11
<211> LENGTH: 873
<212> TYPE: DNA
<213> ORGANISM: Artificial Sequence
<220> FEATURE:
<223> OTHER INFORMATION: Clone 2

<400> SEQUENCE: 11

```
atgtgtgtgg tgtgtgggtg tgtgtgggtg tgtgggtgtg tgggtaggga acagggta       60 atcacccacc catcgaaagc tacatataag gaacgtgctg ctactcatcc tagtcctgtt    120
gctgccaagc tatttaatat catgcacgaa agcaaacaa acttgtgtgc ttcattggat     180
gttcgtacca ccaaggaatt actggagtta gttgaagcat taggtcccaa aatttgttta    240
ctaaaaacac atgtggatat cttgactgat ttttccatgg agggcacagt taagccgcta    300
aaggcattat ccgccaagta caatttttta ctcttcgaag acagaaaatt tgctgacatt    360
ggtaatacag tcaaattgca gtactctgcg ggtgtataca gaatagcaga atgggcagac    420
attacgaatg cacacggtgt ggtgggccca ggtattgtta gcggtttgaa gcaggcggca    480
gaagaagtaa caaaggaacc tagaggcctt ttgatgttag cagaattgtc atgcaagggc    540
tccctatcta ctggagaata tactaagggt actgttgaca ttgcgaagag cgacaaagat    600
```

| tttgttatcg gctttattgc tcaaagagac atggggtggaa gagatgaagg ttacgattgg | 660 |
| ttgattatga cacccggtgt gggtttagat gacaagggag acgcattggg tcaacagtat | 720 |
| agaaccgtgg atgatgtggt ctctacagga tctgacatta ttattgttgg aagaggacta | 780 |
| tttgcaaagg gaagggatgc taaggtagag ggtgaacgtt acagaaaagc aggctgggaa | 840 |
| gcatatttga agatgcgg ccagcaaaac taa | 873 |

<210> SEQ ID NO 12
<211> LENGTH: 903
<212> TYPE: DNA
<213> ORGANISM: Artificial Sequence
<220> FEATURE:
<223> OTHER INFORMATION: Clone 3

<400> SEQUENCE: 12

| atgtgtgtgg tgtgtgggtg tgtgtgggtg tgtgggtgtg tgggtaggga taacagggta | 60 |
| atcacccacc acacacaccc acacacacca cacacccacc catcgaaagc tacatataag | 120 |
| gaacgtgctg ctactcatcc tagtcctgtt gctgccaagc tatttaatat catgcacgaa | 180 |
| aagcaaacaa acttgtgtgc ttcattggat gttcgtacca ccaaggaatt actggagtta | 240 |
| gttgaagcat taggtcccaa aatttgttta ctaaaaacac atgtggatat cttgactgat | 300 |
| ttttccatgg agggcacagt taagccgcta aaggcattat ccgccaagta caatttttta | 360 |
| ctcttcgaag acagaaaatt tgctgacatt ggtaatacag tcaaattgca gtactctgcg | 420 |
| ggtgtataca aatagcaga atgggcagac attacgaatg cacacggtgt ggtgggccca | 480 |
| ggtattgtta gcggtttgaa gcaggcggca gaagaagtaa caaaggaacc tagaggcctt | 540 |
| ttgatgttag cagaattgtc atgcaagggc tccctatcta ctggagaata tactaagggt | 600 |
| actgttgaca ttgcgaagag cgacaaagat tttgttatcg gctttattgc tcaaagagac | 660 |
| atgggtggaa gagatgaagg ttacgattgg ttgattatga cacccggtgt gggtttagat | 720 |
| gacaagggag acgcattggg tcaacagtat agaaccgtgg atgatgtggt ctctacagga | 780 |
| tctgacatta ttattgttgg aagaggacta tttgcaaagg gaagggatgc taaggtagag | 840 |
| ggtgaacgtt acagaaaagc aggctgggaa gcatatttga agatgcgg ccagcaaaac | 900 |
| taa | 903 |

<210> SEQ ID NO 13
<211> LENGTH: 873
<212> TYPE: DNA
<213> ORGANISM: Artificial Sequence
<220> FEATURE:
<223> OTHER INFORMATION: Clone 4

<400> SEQUENCE: 13

| atgtgtgtgg tgtgtgggtg tgtgtgggtg tgtgggtgtg tgggtaggga taacagggta | 60 |
| atcacccacc catcgaaagc tacatataag gaacgtgctg ctactcatcc tagtcctgtt | 120 |
| gctgccaagc tatttaatat catgcacgaa aagcaaacaa acttgtgtgc ttcattggat | 180 |
| gttcgtacca ccaaggaatt actggagtta gttgaagcat taggtcccaa aatttgttta | 240 |
| ctaaaaacac atgtggatat cttgactgat ttttccatgg agggcacagt taagccgcta | 300 |
| aaggcattat ccgccaagta caatttttta ctcttcgaag acagaaaatt tgctgacatt | 360 |
| ggtaatacag tcaaattgca gtactctgcg ggtgtataca aatagcaga atgggcagac | 420 |
| attacgaatg cacacggtgt ggtgggccca ggtattgtta gcggtttgaa gcaggcggca | 480 |
| gaagaagtaa caaaggaacc tagaggcctt ttgatgttag cagaattgtc atgcaagggc | 540 |

```
tccctatcta ctggagaata tactaagggt actgttgaca ttgcgaagag cgacaaagat      600
tttgttatcg gctttattgc tcaaagagac atgggtggaa gagatgaagg ttacgattgg      660
ttgattatga cacccggtgt gggtttagat gacaagggag acgcattggg tcaacagtat      720
agaaccgtgg atgatgtggt ctctacagga tctgacatta ttattgttgg aagaggacta      780
tttgcaaagg gaagggatgc taaggtagag ggtgaacgtt acagaaaagc aggctgggaa      840
gcatatttga gaagatgcgg ccagcaaaac taa                                   873
```

TELOMERATOR-A TOOL FOR CHROMOSOME ENGINEERING

CROSS-REFERENCE TO RELATED APPLICATIONS

This application is a 35 U.S.C. § 371 U.S. national entry of International Application PCT/US2014/021158, having an international filing date of Mar. 6, 2014, which claims the benefit of U.S. Provisional Application No. 61/773,206, filed Mar. 6, 2013, the content of each of the aforementioned applications is herein incorporated by reference in their entirety.

STATEMENT OF GOVERNMENTAL INTEREST

This invention was made with government support under grant number MCB1026068, awarded by the National Science Foundation. The government has certain rights in the invention.

FIELD OF THE INVENTION

The present invention relates to the field of chromosome engineering. More specifically, the present invention provides methods and compositions useful for inducibly linearizing circular DNA molecules in vivo in yeast.

INCORPORATION-BY-REFERENCE OF MATERIAL SUBMITTED ELECTRONICALLY

This application contains a sequence listing. It has been submitted electronically via EFS-Web as an ASCII text file entitled "P12280-02_Sequence_Listing.txt." The sequence listing is 8,462 bytes in size, and was created on Mar. 6, 2014. It is hereby incorporated by reference in its entirety.

BACKGROUND OF THE INVENTION

Chromosome engineering is the study of genetic modifications that affect large segments of chromosomes. Top down approaches start with pre-existing chromosomes and modify them in vivo by introducing, for instance, large deletions, inversions, or duplications. Bottom up approaches, on the other hand, attempt to design and build chromosomes de novo. In either case, we need a strong understanding not only of chromosomal features that confer mitotic stability, including centromeres, telomeres, and origins of replication, but also the effect of the spatial relationships of these elements with one another and with other chromosomal features like genes.

The *Saccharomyces cerevisiae* genome is an excellent platform to develop tools for chromosome engineering given the ease of genetic manipulation and similarity to higher eukaryotes. The *S. cerevisiae* genome is composed of 12 Mb of DNA inherited via 16 linear chromosomes ranging in size from 270 kb to over 1 Mb (1). Two important cis elements are required to maintain chromosome stability through mitosis and meiosis: compact point centromeres (~125 bp) ensure faithful segregation of sister chromatids (2), and conserved telomere sequences protect the ends of each chromosome and guarantee the maintenance of chromosome length during replication (3, 4). With these elements intact, many lines of evidence indicate budding yeast tolerates a high degree of chromosomal modifications without affecting viability, for instance: (a) the largest yeast chromosome (IV) can be sub-divided into 11 separate mini-chromosomes (5); (b) more than 500 kb, including 247 non-essential genes, can be deleted in a single haploid strain (6); (c) any of the 16 chromosomes can be individually destabilized in a diploid cell to generate a chromosomal complement of 2n−1 (7); (d) a designer, synthetic chromosome arm, synIXR, was shown to power growth of budding yeast in the absence of the native chromosome sequence (8).

SUMMARY OF THE INVENTION

The present invention is based, at least in part, on the development of compositions and methods to inducibly convert circular DNA molecules in yeast into stably maintained linear chromosomes. We call this genetic system "The Telomerator." In brief, we can introduce a "telomerator cassette" by homologous recombination into any circular DNA intended to be linearized, in principle, at any position. The cassette encodes a selectable marker gene sequence interrupted by an intron that harbors a homing endonuclease recognition site such as I-SceI. The recognition site is flanked by telomere seed sequences (TeSS), short stretches of minimal yeast telomere sequences. When the endonuclease is inducibly expressed, circular DNA is efficiently linearized and subsequently stably maintained due to the presence of the terminal TeSSs.

Accordingly, in one aspect, the present invention provides a telomerator cassette. In one embodiment, a telomerator cassette comprises a nucleic acid encoding a selectable marker, wherein the nucleic acid encoding a selectable marker comprises an intron comprising an endonuclease recognition site flanked by telomere seed sequences. In a specific embodiment, the intron is the ACT1 intron. A telomerator cassette can also be referred to as a cassette, an expression cassette, a nucleic acid construct, a construct or simply, a composition.

In another embodiment, a telomerator cassette comprises a nucleic acid encoding a selectable marker, wherein the nucleic acid encoding a selectable marker comprises an endonuclease recognition site flanked by telomere seed sequences. The site and flanking sequences are inserted in-frame into the nucleic acid sequence encoding the selectable marker to allow expression. In a specific embodiment, the endonuclease recognition site flanked by telomere seed sequences comprises SEQ ID NO:4. In another embodiment, a telomerator cassette comprises a nucleic acid encoding a selectable marker, wherein the nucleic acid encoding the selectable marker comprises an endonuclease recognition site flanked by telomere seed sequences such that the selectable marker retains its function. In a further embodiment, a telomerator cassette comprises a nucleic acid encoding a selectable marker, wherein the nucleic acid encoding a selectable marker comprises the original marker sequence operably linked as a protein fusion with an endonuclease recognition site flanked by telomere seed sequences.

In one embodiment, the marker is an auxotrophic marker. Auxotrophic markers can include, but are not limited to, LEU2, URA3, TRP1, MET15, LYS1, and HIS3. In a specific embodiment, the auxotrophic marker is the URA3 gene. In another embodiment, the marker is a drug selection marker and may include, but is not limited to, nourseothrecin (NAT), geneticin, and hygromycin In particular embodiments, the selectable marker is both selectable and counterselectable. Examples in yeast include URA3, LYS2 and TRP1, counterselectable using 5-fluoroorotic acid, alpha-amino-adipate, and 5-fluoro-anthranilic acid, respectively. In other embodiments, a counterselectable marker, e.g., CYH2 (counterselectable on cycloheximide), can be fused to any other selectable marker by joining the two open reading frames in such a way that both moieties are functional.

In another embodiment, the endonuclease recognition site is specific for I-SceI. In a more specific embodiment, the I-SceI endonuclease recognition site comprises SEQ ID NO:2. In other embodiments, the endonuclease may comprise restriction endonucleases, Zinc finger nucleases, TALENs or other meganucleases.

In certain embodiments, the telomere seed sequences comprise minimal telomere seed sequences. In general, the telomere seed sequences for yeast comprise $[(TG_{(1-3)})_{16} \cdots (C_{(1-3)}A)_{16}]$. In a specific embodiment, the telomere seed sequences comprise SEQ ID NO:1 and SEQ ID NO:3.

In particular embodiments, a circular chromosome comprises a telomerator cassette described herein. In other embodiments, a eukaryotic host cell comprises a circular chromosome of the present invention. In a specific embodiment, the eukaryote is yeast. In a more specific embodiment, the yeast is *S. cerevisiae*. In other embodiments, the yeast is *Hansenula polymorpha*, *Pichia pastoris* or *Schizosaccharomyces pombe*.

In specific embodiments, the eukaryotic host cell comprises a vector encoding the endonuclease under the control of an inducible promoter. In a particular embodiment, the inducible promoter is the GAL1 promoter. Other promoters can include, but are not limited to, pMET15, pCUP2, other pGAL sequences, and TetON/TetOFF systems.

In a specific embodiment, a telomerator cassette of the present invention comprises a nucleic acid that encodes the auxotrophic marker URA3, wherein the nucleic acid comprises an intron that comprises the I-SceI endonuclease recognition site flanked by telomere seed sequences. In a more specific embodiment, the telomere seed sequences comprise SEQ ID NO:1 and SEQ ID NO:3. In another embodiment, the I-SceI endonuclease recognition site comprises SEQ ID NO:2. A circular chromosome can comprise a telomerator cassette described herein. In another embodiment, a yeast host cell comprises a circular chromosome described herein. The yeast host cell may comprise a vector encoding the I-SceI endonuclease under the control of an inducible promoter. More specifically, the inducible promoter can be the GAL1 promoter.

In one embodiment, a yeast host cell comprises a circular chromosome comprising a telomerator cassette encoding a selectable marker, wherein the nucleic acid encoding the selectable marker comprises an intron that comprises an endonuclease recognition site flanked by telomere seed sequences; and a vector encoding the endonuclease under the control of an inducible promoter. In a specific embodiment, the selectable marker is an auxotrophic marker. In a more specific embodiment, the auxotrophic marker is the URA3 gene. In the yeast host the endonuclease recognition site is specific for I-SceI. More specifically, the I-SceI endonuclease recognition site comprises SEQ ID NO:2. Moreover, the telomere seed sequences can comprise SEQ ID NO:1 and SEQ ID NO:3.

In another aspect, the present invention provides methods for chromosome engineering. In one embodiment, a method for engineering a circular chromosome capable of being inducibly linearized comprises the step of integrating a telomerator cassette into a circular chromosome, wherein the telomerator cassette comprises a nucleic acid encoding a selectable marker, wherein the nucleic acid encoding a selectable marker comprises an intron comprising an endonuclease recognition site flanked by telomere seed sequences. In a specific embodiment, the integrating step is accomplished by transforming a telomerator cassette into a host cell comprising the circular chromosome. In another embodiment, the host cell comprises a vector encoding the endonuclease under the control of an inducible promoter.

DETAILED DESCRIPTION OF THE INVENTION

Figure 1:
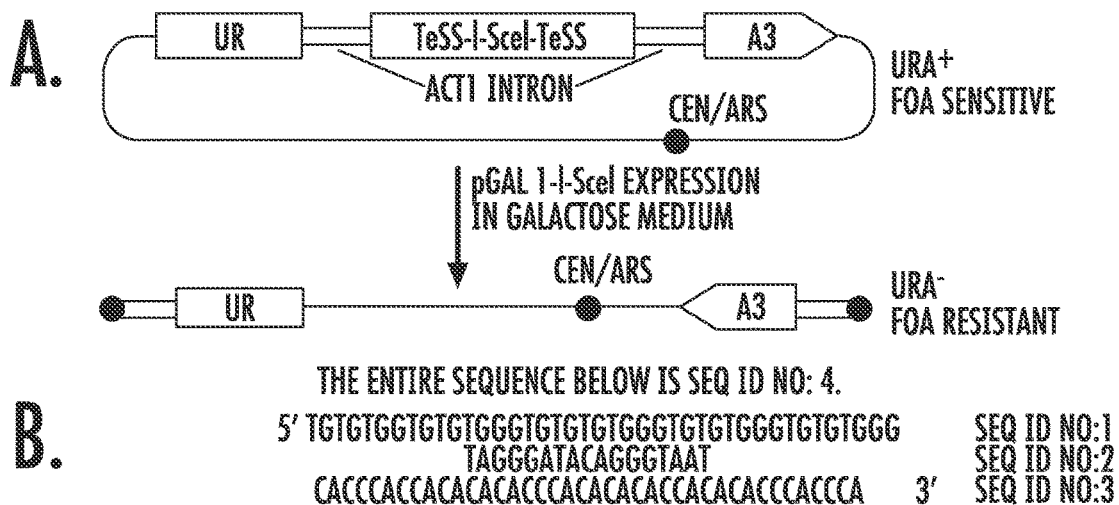
FIG. 1: Telomerator Design and Function. (A) The telomerator encodes a selectable URA3 gene sequence interrupted by an intron (ACT1 intron) that harbors a homing endonuclease recognition site (I-SceI). The recognition site is flanked by telomere seed sequences (TeSS). The telomerator cassette is encoded on a circular DNA molecule yielding cells that grow on medium lacking uracil (Ura$^+$) but are sensitive to the uracil counterselection drug Foa, assuming the circular DNA molecule encodes at least one essential genetic part. Expression of I-SceI, under the control of the GAL1 promoter (pGAL1), is induced by growth in galactose medium. Cells harboring newly linearized molecules should no longer grow on plates lacking uracil (Ura$^-$) and moreover should be resistant to Foa (Foa$^R$). (B) Sequence of the TeSS-I-SceI-TeSS region of the telomerator.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Chromosome engineering is an emerging focus in the fields of systems biology, genetics, synthetic biology, and the functional analysis of genomes. Here we describe the 'telomerator', a new synthetic biology device designed to inducibly linearize circular DNA molecules in vivo in *Saccharomyces cerevisiae*. To demonstrate the functionality and utility of the telomerator, we generate linear variants of a synthetic yeast chromosome originally built as a circular molecule, synIXR BAC. By circularly permuting synIXR BAC using the telomerator, we generated an array of 53 different linearized chromosome structures, many of which confer novel phenotypic properties. This tool offers a new way to study the effect of gene placement on chromosomes (i.e. telomere proximity), the essentiality of 3' non-coding regions of genes, and the plasticity of gene order and chromosome structure on cell fitness. The telomerator will be an important tool to generate artificial, linear chromosomes in yeast and the concept could be extended to other eukaryotes including mammals and human cells.

The term "nucleic acid" or "polynucleotide" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the nucleic acid can comprise sugars and phosphate groups (as may typically be found in RNA or DNA), or modified or substituted sugar or phosphate groups. Alternatively, the backbone of the nucleic acid can comprise a polymer of synthetic subunits such as phosphoramidates and thus can be an oligodeoxynucleoside phosphoramidate ($P-NH_2$) or a mixed phosphoramidate-phosphodiester oligomer. In addition, a double-stranded nucleic acid can be obtained from the single stranded nucleic acid product of chemical synthesis either by synthesizing the complementary strand and annealing the strands under appropriate conditions, or by synthesizing the complementary strand de novo using a DNA polymerase with an appropriate primer.

The following are non-limiting examples of nucleic acids: a gene or gene fragment, exons, introns, mRNA, tRNA, rRNA, ribozymes, cDNA, recombinant nucleic acids, branched nucleic acids, plasmids, vectors, isolated DNA of any sequence, isolated RNA of any sequence, nucleic acid probes, and primers. A nucleic acid may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A nucleic acid may be further modified after polymerization, such as by conjugation with a labeling component. Other types of modifications included in this definition are caps, substitution of one or more of the naturally occurring nucleotides with an analog, and introduction of means for attaching the nucleic acid to proteins, metal ions, labeling components, other nucleic acids, or a solid support.

As used herein, the term "operably linked" means that nucleic acid sequences or proteins are operably linked when placed into a functional relationship with another nucleic acid sequence or protein. For example, a promoter sequence is operably linked to a coding sequence if the promoter promotes transcription of the coding sequence. As a further example, a repressor protein and a nucleic acid sequence are operably linked if the repressor protein binds to the nucleic acid sequence. Additionally, a protein may be operably linked to a first and a second nucleic acid sequence if the protein binds to the first nucleic acid sequence and so influences transcription of the second, separate nucleic acid sequence. Generally, "operably linked" means that the DNA sequences being linked are contiguous, although they need not be, and that a gene and a regulatory sequence or sequences (e.g., a promoter) are connected in such a way as to permit gene expression when the appropriate molecules (e.g., transcriptional activator proteins—transcription factors—or proteins which include transcriptional activator domains) are bound to the regulatory sequence or sequences.

The term "plasmid" refers to an extrachromosomal circular DNA capable of autonomous replication in a given cell. In certain embodiments, the plasmid is designed for amplification and expression in bacteria. Plasmids can be engineered by standard molecular biology techniques. See Sambrook et al., Laboratory Manual, Cold Spring Harbor Laboratory Press, Cold Spring Harbor (1989), N.Y. The term "expression vector" is used interchangeably herein with the term "plasmid" and refers to a recombinant DNA molecule containing a desired coding sequence and appropriate nucleic acid sequences necessary for expression of the operably linked coding sequence (e.g. an insert sequence that codes for a product) in a particular host cell. Nucleic acid sequences necessary for expression in prokaryotes usually include a promoter, an operator (optional), and a ribosome binding site, often along with other sequences.

The term "promoter" refers to the DNA region, usually upstream of the coding sequence of a gene or operon, which binds RNA polymerase and directs the enzyme to the correct transcriptional start site.

The terms "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can for example be a homing endonuclease (Paques et al., Curr Gen Ther. 2007 7:49-66), a chimeric Zinc-Finger nuclease (ZFN) resulting from the fusion of engineered zinc-finger domains with the catalytic domain of a restriction enzyme such as FokI (Porteus et al., Nat Biotechnol. 2005 23:967-973) or a chemical endonuclease (Arimondo et al., Mol Cell Bioi. 2006 26:324-333; Simon et al., NAR 2008 36:3531-3538; Eisenschmidt et al., NAR 2005 33:7039-7047; Cannata et al., PNAS 2008 105:9576-9581). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer Ann NY Acad Sci 2005 1058: 151-61). Such chemical endonucleases are considered to fall within the scope of the term "endonuclease" according to the present invention. Also within the scope of the present invention is intended any fusion between molecules able to bind DNA specific sequences and agent/reagent/chemical able to cleave DNA or interfere with cellular proteins implicated in the double strand break (DSB) repair (Majumdar et al., J. Bioi. Chem 2008 283, 17:11244-11252; Liu et al. NAR 2009 37:6378-6388); as a non-limiting example such a fusion can be constituted by a specific DNA-sequence binding domain linked to a chemical inhibitor known to inhibit re-ligation activity of a topoisomerase after DSB cleavage. Endonucleases can comprise a homing endonuclease, also known under the name of meganuclease. The term "meganuclease" refers to an endonuclease having a double-stranded DNA target sequence of about 12 to about 45 base pairs (bp). Such homing endonucleases are well-known to the art (see e.g. Stoddard, Quarterly Reviews of Biophysics, 2006, 38:49-95). Homing endonucleases recognize a DNA target sequence and generate a single- or double-strand break. Homing endonucleases are highly specific, recognizing DNA target sites ranging from 12 to 45 base pairs (bp) in length, usually ranging from about 14 to about 40 bp in length. The homing endonuclease according to the invention may for example correspond to a LAGLIDADG endonuclease, to a HNH endonuclease, or to a GIY-YIG endonuclease. In certain embodiments, a meganuclease is either a dimeric enzyme, wherein each domain is on a monomer or a monomeric enzyme comprising the two domains on a single polypeptide.

Endonucleases according to the invention can also be derived from TALENs, a new class of chimeric nucleases using a FokI catalytic domain and a DNA binding domain derived from Transcription Activator Like Effector (TALE), a family of proteins used in the infection process by plant pathogens of the *Xanthomonas* genus (Boch, Scholze et al. 2009; Moscou and Bogdanove 2009; Christian, Cermak et al., 2010; Li, Huang et al., 2011) (Boch, Scholze et al., 2009; Moscou and Bogdanove 2009; Christian, Cermak et al., 2010; Li, Huang et al., 2010). The functional layout of a FokI-based TALE-nuclease (TALEN) is essentially that of a ZFN, with the Zinc-finger DNA binding domain being replaced by the TALE domain. As such, DNA cleavage by a TALEN requires two DNA recognition regions flanking an unspecific central region. Endonucleases encompassed in the present invention can also be derived from TALENs. An endonuclease according to the present invention can be derived from a TALE-nuclease (TALEN), i. e. a fusion between a DNA-binding domain derived from a Transcription Activator Like Effector (TALE) and one or two catalytic domains. In other embodiments, CRISPR/Cas systems may be used. See Mali P, Yang L, Esvelt K M, Aach J, Guell M, Dicarlo J E, Norville J E, Church G M: RNA-guided human genome engineering via Cas9. Science 2013; Cong L, Ran F A, Cox D, Lin S, Barretto R, Habib N, Hsu P D, Wu X, Jiang W, Marraffini L A, Zhang F: Multiplex genome engineering using CRISPR/Cas systems. Science 2013; Cho S W, Kim S, Kim J M, Kim J S: Targeted genome engineering in human cells with the Cas9 RNA-guided endonuclease. Nat Biotechnol 2013; Hwang W Y, Fu Y, Reyon D, Maeder M L, Tsai S Q, Sander J D, Peterson R T, Yeh J R, Joung J K: Efficient genome editing in zebrafish using a CRISPR-Cas system. Nat Biotechnol 2013; and Jiang W, Bikard D, Cox D, Zhang F, Marraffini L A: RNA-guided editing of bacterial genomes using CRISPR-Cas systems. Nat Biotechnol 2013.

As used herein, a "selectable marker" refers to a phenotypic trait conferred on transformed cells that protects them from a selective agent in their environment, i.e., the growth media. Examples of selectable markers include, but are not limited to, antibiotic resistance markers (e.g., genes encoding resistance to kanamycin, ampicillin, chloramphenicol, gentamycin, or tetracycline), metabolic markers (e.g., amino acid synthesis genes or transfer RNA genes) and auxotrophic markers.

As used herein, the term "vector" refers to a nucleic acid construct designed for transduction/transfection of one or more cell types. Vectors may be, for example, "cloning vectors" which are designed for isolation, propagation and replication of inserted nucleotides, "expression vectors"

which are designed for expression of a nucleotide sequence in a host cell. The term "replication" means duplication of a vector.

Any yeast cell can be used in the methods of the present invention. In particular embodiments, a yeast species within the genus of *Saccharomyces*, particularly *Saccharomyces cerevisiae*, are used. Other examples of suitable yeast species include, but are not limited to, *Hansenula polymorpha*, *Pichia pastoris*, and *Schizosaccharomyces pombe*. Indeed, numerous yeast strains or derivative strains are known in the art. The application and optional modification of such strains for purposes of the present invention should be apparent to a skilled artisan apprised of the present disclosure.

Our goal was to systematically perturb order and orientation of genetic elements on linear chromosomes in *S. cerevisiae*. To achieve this, we have developed the telomerator, a genetic tool that can inducibly linearize circular DNA molecules in vivo. We use the telomerator to circularly permute the synIXR synthetic chromosome, which is encoded as a bacterial artificial chromosome (BAC, herein referred to synIXR BAC). Our results support that telomerator-induced linearization generates linear chromosomes with functional telomeres on which heterochromatin is fully established.

At least two previous methods have been used to construct artificial linear chromosomes in yeast. First, non-native chromosomes were generated by in vitro ligation of synthetic telomere sequences onto linear DNA followed by transformation and selection in yeast (20, 21). This approach overcomes the complicating factor that linear DNA molecules cannot be replicated in *E. coli* and can therefore be difficult to construct. Secondly, a circular derivative of chromosome three (22) was linearized by integrating into it synthetic telomere sequences; over time these sequences resolved in vivo to generate a linear molecule (23). Together these studies shed light on important features about the mitotic stability of chromosomes. First, the overall length of linear DNA molecules is a major contributing factor to mitotic stability (16, 20, 21, 23). Second, the spatial relationship between the centromere and telomeres has very little impact on mitotic stability (16, 23). Finally, X and Y' elements located in subtelomeric regions of native *S. cerevisiae* chromosomes have little or no impact on mitotic stability (23).

The telomerator represents a new and convenient way to linearize circular DNA molecules in vivo in *S. cerevisiae* and can be applied to the construction of artificial chromosomes. Here we demonstrate its utility by circularly permuting a pre-existing circular synthetic chromosome in yeast—synIXR. In terms of chromosome engineering, the telomerator presents four major advantages over the approaches described above: (i) the use of telomere seed sequences that correspond to native yeast telomeres; (ii) the ease with which a telomerator construct can be PCR amplified and thus integrated at multiple unique loci; (iii) the method gives virtually 100% correct clones with no requirement for cumbersome screening approaches; and (iv) the inducible control over timing of linearization in vivo.

Linear Permutations of synIXR.

In our work, we linearized circular chromosomes to generate minimal telomere sequences. Based on the SIR2-dependent phenotypes observed, we conclude that heterochromatin is forming on the linearized chromosomes. In native chromosomes, subtelomeric sequences can buffer these effects, as can insulators. Future telomerator designs could incorporate such elements.

With the exception of effects on gene expression, the panel of permuted chromosomes displays surprisingly little variation in behavior, suggesting that the relative placement of telomeres and centromeres in *S. cerevisiae* is quite flexible. For instance, linearization at either YIL001 W or YIR001C produces telocentric versions of synIXR with only ~1 kb separating the centromere from a telomere; that these permutations exhibit no apparent growth defect is consistent with previous work suggesting telocentric chromosomes in budding yeast are mitotically stable (16, 23).

Other Applications for Telomerator.

The telomerator provides a flexible new strategy to aid in the construction and expression of supernumerary chromosomes encoding non-native pathways that give a multitude of new functions to the cell. In principle, this technology can be extended to other eukaryotic organisms, especially those with point/small centromeres like budding yeast. Applying the telomerator to chromosome engineering in mammalian cells will be more challenging as 'regional' mammalian centromeres can extend for hundreds of kilobases and include repetitive sequences. Artificially generated human minichromosomes, existing as either linear or circular constructs, have been described and they may serve as a starting point for mammalian artificial chromosome engineering (24-30). We ultimately envision such artificial chromosomes as valuable platforms for gene targeting that will allow delivery of large DNAs to recipient cells and provide a means by which to investigate the incorporation of complex segments of DNA encoding networks and pathways.

Prospects for Telomerators in Other Systems/Organisms.

The linearization function of the telomerator can obviously be achieved with a wide variety of restriction endonucleases, Zinc finger nucleases, TALENs or meganucleases besides I-SceI. One important consideration is that the recognition sequence of the enzyme must be sufficiently rare within the sequence of the host genome (i.e., no or few existing sites) to work without causing "collateral damage" in the rest of the genome. In this regard the I-SceI site is not present in yeast nuclear genome (31). A wide variety of selectable/counterselectable markers could also be employed.

Another approach to introduce the Telomerator sequence into a circular DNA molecule for linearization is to include the TeSS-I-SceI-TeSS sequence as part of the protein coding sequence of the selectable marker. In such embodiments, the TeSS-I-SceI-TeSS sequence is "in-frame" with the selectable marker sequence (i.e., a multiple of 3) such that the resulting protein translation would not be truncated. The TeSS-I-SceI-Tess sequence is inserted into the selectable marker in a position that would not disrupt function of the resulting protein product. Shorter TeSSs have been described in the literature (Yamagishi 2008 Appl Microbiol Biotechnol 79:699-706), and could be employed in this so-called Telomerator-fusion protein model in order to increase the stability of the highly repetitive TeSS sequences.

This work should be easily expandable to other yeast species. This is relevant in the academic setting, where fungal species other than *S. cerevisiae* are becoming increasingly commonplace (i.e., *Ashbya gossypii, Candida glabrata, Pichia pastoris* etc.). Furthermore, many yeast species are used industrially, exploiting unique properties beneficial to the process of interest (e.g., *P. pastoris*, high-level secreted protein production; *A. gossypii*, riboflavin production). Similarly, the approach could almost certainly be expanded to other eukaryotic microorganisms such as algae, and potentially to various tissue culture cells.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Construction of the Telomerator.

The TeSS-I-SceI sequence was introduced by one-step isothermal assembly (32) into the unique XhoI site encoded centrally within the ACT1 intron that had been previously transplanted into URA3(12). Specifically, the TeSS-I-SceI-TeSS sequence (5'TGTGTGGTGTGTGGGTGTGT-GTGGGTGTGTGGGTGTGTGGGTAGGGATAACAG GGTAATCACCCACCCACACACACCCACACACACCA-CACACCCACCCA3') (SEQ ID NO:4) flanked by 40 bp corresponding to sequence on either side of the XhoI site was ordered from IDT as an Ultramer. This sequence was exponentially amplified using external primers (F 5'ATC-CATTTAACTGTAAGAAGAATTGC3' (SEQ ID NO:5); R 5'GGAGAGTGAAAAATAGTAAAAAAAGGT3' (SEQ ID NO:6)). Expression of the URA3-intronACT1-TeSS-I-Sce-I-TeSS-intronACT1-URA3 cassette was verified by functional complementation assay as described in the text.

Integration of Telomerator into synIXR BAC.

Figure 6:
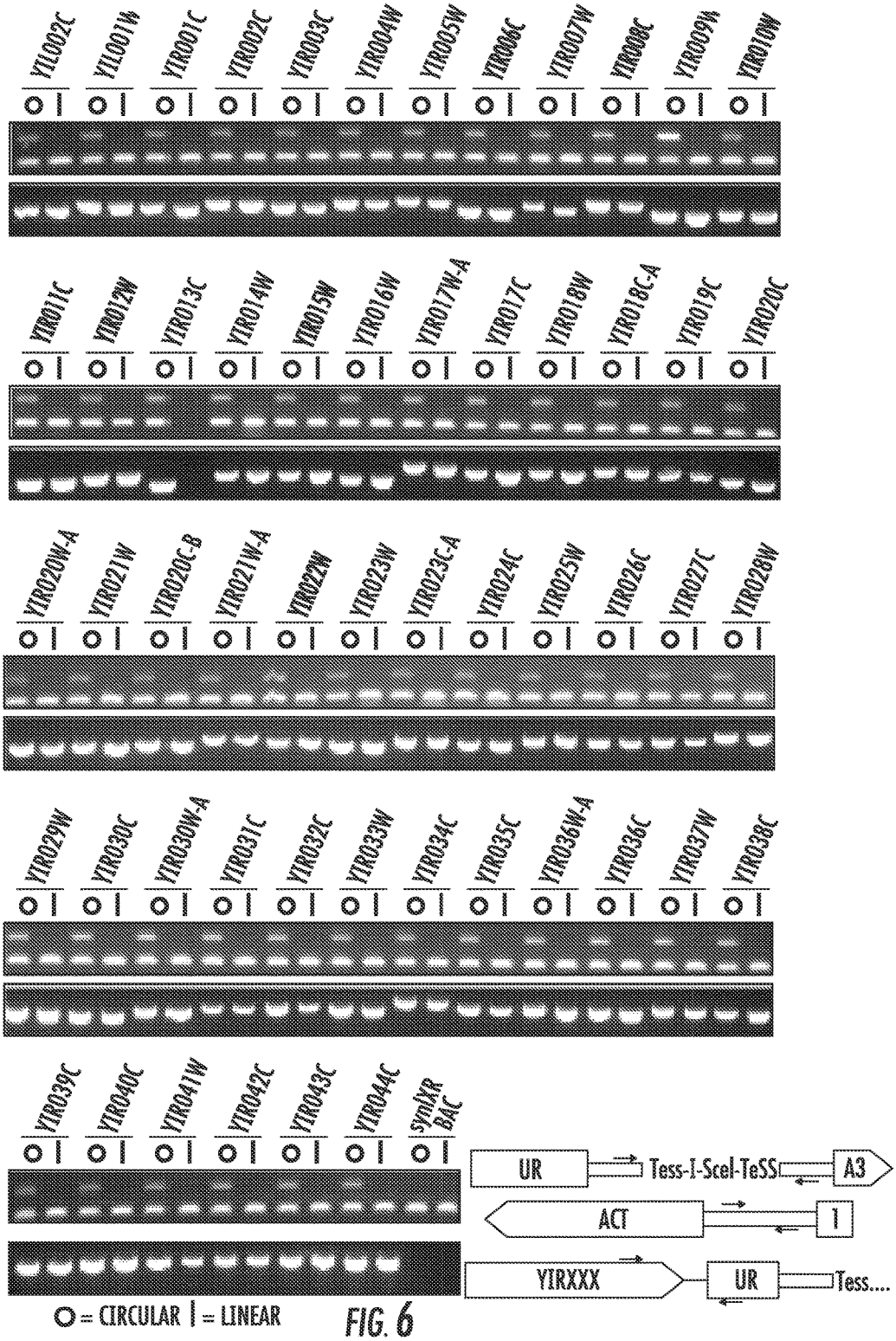
FIG. 6: PCR confirmation of integration and circular/linear status. All permutations were tested, pre- and post-linearization (circular and linear, respectively), by PCR using two primer sets. First, integration was confirmed using a gene-specific primer in combination with a primer that annealed within the telomerator (green arrows). These primers confirmed the presence of this region in either the linear or circular conformation of synIXR in all strains. Secondly, a primer pair designed to anneal to the ACT1 intron (red arrows) was used. This primer pair amplifies a product from the endogenous ACT1 intron at its native locus on chromosome six, as well as from an intact telomerator cassette. Following growth in galactose, absence of this band is consistent with linearization.

Primers were designed to bind upstream of the URA3 promoter (5'CCCGGGGGATCCGGTGATTG3') (SEQ ID NO:7) and downstream of the URA3 terminator (5'CCAAAGCTGGAGCTCCACCG3') (SEQ ID NO:8) on the telomerator construct. 50 bp corresponding to either side of each unique integration site was then appended to these two primers. Standard PCR conditions were used to amplify the telomerator, which was then transformed into a synIXR BAC containing strain (yJS587 (8)). Integration was confirmed with a location specific primer in combination with a primer internal to the URA3 promoter sequence (FIG. 6).

Linearization of synIXR.

The pGAL1-I-SceI sequence was subcloned from a pre-existing plasmid (33) into the yeast shuttle vector pRS413 (14) at the SalI recognition site. This construct was transformed into strains to be linearized and selected on medium lacking histidine (SC-His). Linearization was induced in liquid culture in synthetic medium lacking histidine with 2% galactose for 24 hours. Strains were then transferred onto synthetic complete solid medium supplemented with Foa and extra uracil. Each strain was subjected to single round of colony purification on YPD medium and single isolates that had lost the pGAL-I-Sce-I construct, confirmed by replica-plating on SC-His, were selected for further analysis. Circular versus linear status of synIXR was tested by PCR using the primers originally designed to amplify the TeSS-I-Sce-I-TeSS ultramer (described above and FIG. 6).

Pulsed Field Gel Electrophoresis.

Full length yeast chromosomes were prepared in agarose plugs as previously described (34). Chromosomes were separated by clamped homogeneous electric field (CHEF) gel electrophoresis using the CHEF-DR III Pulsed Field Electrophoresis Systems (Biorad) with the following settings: 6V/cm, switch time 60-120 seconds over 24 hours, 14° C., 0.5×TBE, 1% gel prepared with low melting point agarose (Lonza, 50100). Gels were stained with 5 ug/ml ethidium bromide in water post-electrophoresis and then imaged.

SIR2 Gene Deletion.

The sir2ΔkanMX locus was amplified from the deletion mutant collection strain (35) using primers ~500 bp flanking the gene deletion and subsequently transformed into the array of permutable strains by selection on YP supplemented with 200 μg/mL geneticin. SIR2 gene deletion was confirmed functionally by confirming the loss of mating proficiency.

Results

Example 1: Telomerator Design and Function/Application

The design of the telomerator includes several different elements (FIG. 1A). Centrally, the telomerator encodes an 18 base pair recognition sequence for the I-SceI homing endonuclease (9, 10). This site is flanked by a pair of convergent telomere seed sequences (TeSS) that encode ~40 bp of conserved yeast telomere repeats $[(TG_{(1-3)})_{16} \ldots (C_{(1-3)}A)_{16}]$ previously shown to serve as a minimal telomeric repeat (11) (FIG. 1B). The entire TeSS-I-SceI-TeSS sequence is encoded within an intron that interrupts the URA3 S. cerevisiae auxotrophic selectable marker coding sequence. Previous work showed that transplantation of the ACT1 gene intron into the middle of the URA3 coding sequence did not disrupt complementation on medium lacking uracil, indicating the mRNA was expressed and the non-native intron correctly spliced prior to translation of the URA3 gene product (12). Thus, the overall design of the telomerator is as follows: 5'-URA3exon1-intronACT1-TeSS-I-SceI-TeSS-intronACT1-URA3exon2-3'.

Expression of the I-SceI homing endonuclease, which recognizes and cleaves the 18 bp I-SceI recognition site, can linearize a circular DNA molecule encoding the telomerator. To facilitate inducible linearization, I-SceI expression can be placed under control of the inducible GAL1 promoter and thus linearization driven specifically by growth in medium containing galactose. Under standard growth conditions in glucose medium, the telomerator cassette should remain intact with cells expressing a functional Ura3 protein, complementing growth of a ura3Δ0 strain on medium lacking uracil. Following growth in galactose, the linearization reaction can be selected on 5-fluoroorotic acid (Foa) medium, which counterselects against URA3+ cells (13); a circular telomerator-containing molecule will grow on medium lacking uracil and die on FOA, but a cell harboring a linearized molecule, in which the URA3 gene component of the telomerator is literally split in two, should display the opposite growth phenotype (Ura⁻, Foa$^R$ [uracil requiring and resistant to Foa]) (FIG. 1A).

Example 2: Telomerator Constructs Complement Growth on Medium Lacking Uracil

Figure 2:
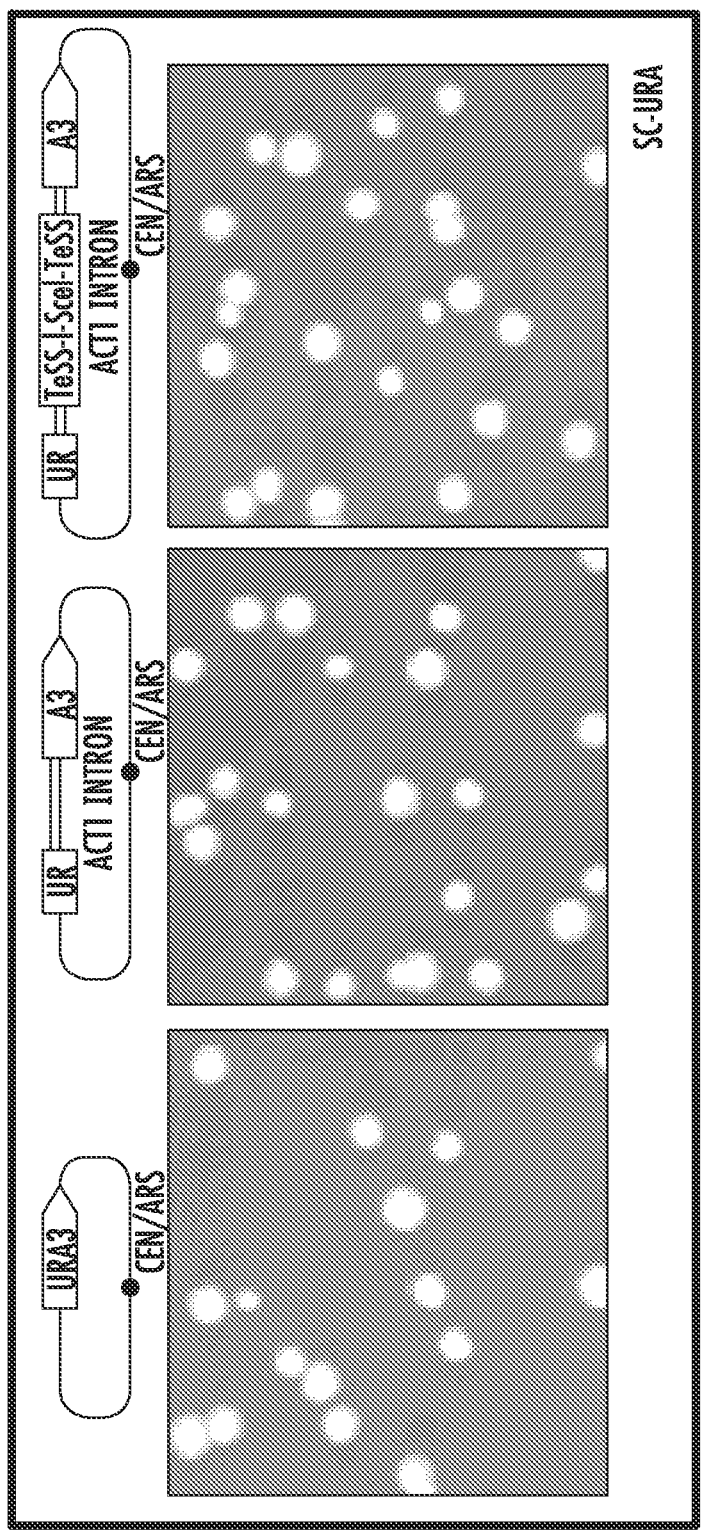
FIG. 2: The telomerator complements yeast cell growth on medium lacking uracil. Plasmids encoding either a native URA3 gene (left), a URA3 gene interrupted by the intron of ACT1 (middle), or a URA3 gene interrupted by a telomerator sequence encoded within the ACT1 intron (right), were transformed into a yeast strain (BY4741) incapable of growing on medium lacking uracil (SC-Ura). Growth of the resulting transformed colonies on SC-Ura was indistinguishable indicating normal expression of the URA3 gene product from the telomerator-encoding construct.

While expression of the URA3 gene interrupted by the ACT1 intron was previously shown to complement growth of ura3 mutants on medium lacking uracil (12), the effect on complementation of further encoding the TeSS-I-SceI-TeSS sequence within the intron was unknown. To test this, we constructed the telomerator cassette in pRS413, a centromere-based yeast shuttle vector encoding the HIS3 selectable marker (14). The telomerator-containing construct was transformed into BY4741, a yeast strain with a complete URA3 deletion (ura3Δ0) (15), and plated on medium lacking uracil. Growth of the resulting transformants was compared to cells transformed with pRS416, another centromere-based yeast shuttle vector encoding a wild type URA3 gene, or a plasmid encoding the URA3exon1-intronACT1-URA3exon2 cassette (12), identical to the telomerator plasmid but lacking the TeSS-I-SceI-TeSS sequence. Growth of cells transformed with any of the three constructs on medium lacking uracil was indistinguishable (FIG. 2). Thus, the presence of the TeSS-I-SceI-TeSS sequence within the ACT1 intron interrupting the URA3 gene does not interfere with growth on medium lacking uracil.

Figure 3:
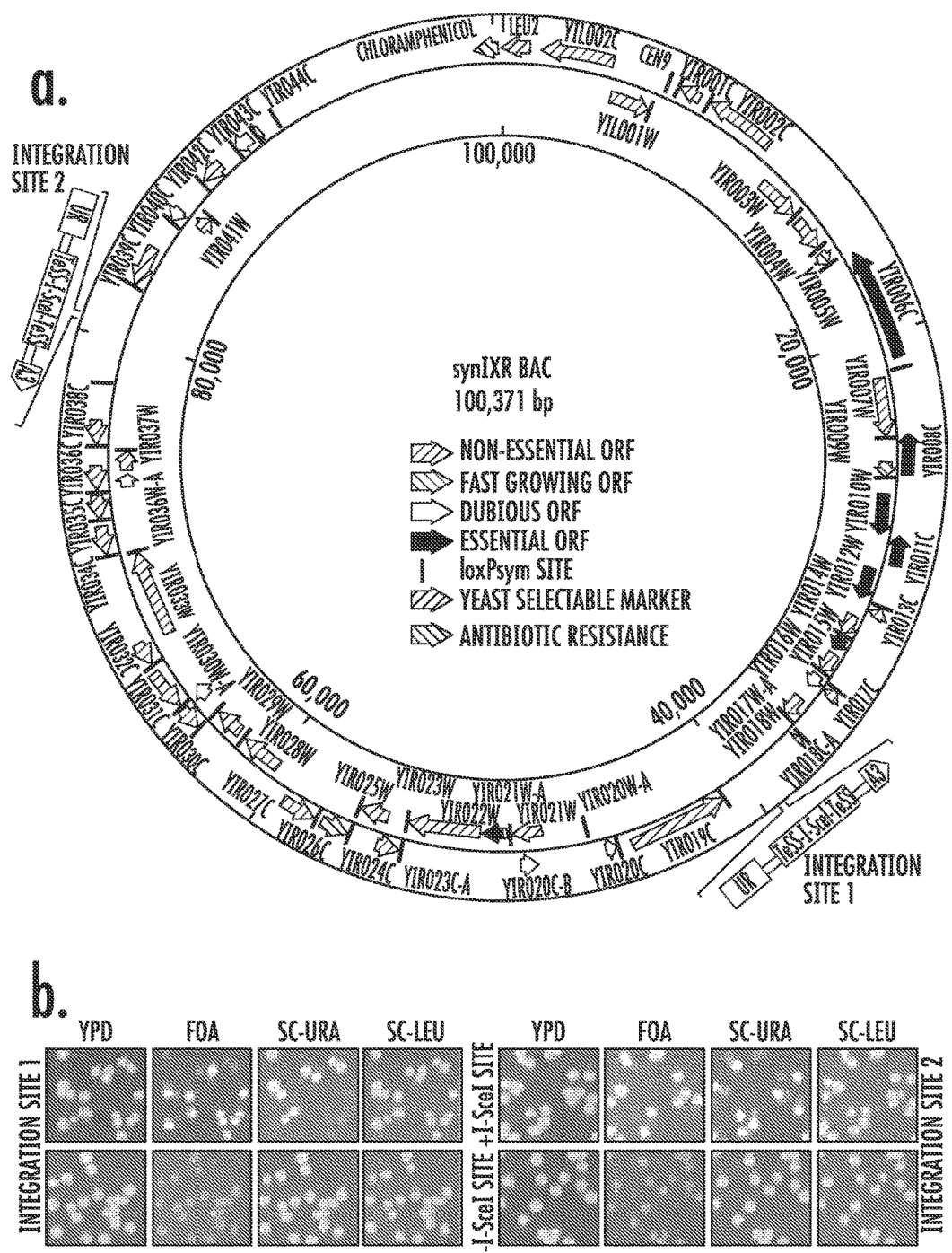
FIG. 3: The telomerator drives in vivo linearization of a synthetic yeast chromosome arm, synIXR BAC. (A) synIXR BAC is a ~100 kb circular chromosome arm that can power a yeast cell. In independent integration experiments, the telomerator cassette was introduced by homologous recombination at two gene-free regions of synIXR BAC as indicated (Integration Site 1, ~40 kb; Integration Site 2, ~80 kb). (B) Following 24 hours of growth in galactose-containing medium to induce expression of I-SceI, single cells from Integration Site 1 (left) and Integration Site 2 (right) were plated on YPD medium, and then replica plated onto synthetic complete medium supplemented with 5'-fluoroorotic acid (Foa), and synthetic complete medium lacking uracil or leucine (SC-Ura and SC-Leu, respectively). Only in cell populations encoding an intact I-SceI recognition sequence as part of the telomerator cassette (+I-SceI, top row) did linearization occur, as assayed by growth on Foa and non-growth on SC-Ura.

Example 3: The Telomerator can Inducibly Linearize Circular DNA Molecules In Vivo Chromosome length has important consequences for mitotic stability as linear chromosomes shorter than 90 kb exhibit markedly decreased stability (16). Therefore, we tested the capacity of the telomerator to linearize circular DNA molecules in vivo using synIXR, a synthetic yeast chromosome arm corresponding to the right arm of chromosome nine previously constructed as a bacterial artificial chromosome (BAC) (8, 17) approximately 100 kb long. SynIXR encodes all 52 genes from the right arm of chromosome 9 (YIR001C-YIR044C), 2 genes from the left arm (YIL001W, YIL002C), the native chromosome 9 centromere (CEN9), a yeast selectable marker (LEU2), plus ~10 kb of BAC vector sequence including the chloramphenicol resistance gene (FIG. 3A). synIXR, which encodes seven essential genes, was previously shown to be mitotically stable in vivo and power yeast cell growth at wild type levels in the absence of the wild type chromosome arm IXR (8). Two 'gene-free' regions of synIXR BAC were chosen as initial integration sites for the telomerator cassette, which was then introduced by homologous recombination to generate two new strains for linearization. Additionally, the URA3exon1-intronACT1-URA3exon2 cassette (12), lacking the TeSS-I-SceI-TeSS sequence, was integrated at the same two positions to generate equivalent, but non-linearizeable control strains. All four strains were transformed with a plasmid expressing pGAL1-I-SceI, grown in galactose medium for 24 hours, and finally ~200 cells were plated on YPD, permissive yeast medium containing dextrose. These plates were replica printed onto medium containing Foa and uracil, or on medium lacking uracil (SC-Ura) or leucine (SC-Leu) (FIG. 3B). At either integration site 1 or 2, in cells expressing the functional telomerator cassette (+I-SceI), ~50% of cells became resistant to growth on Foa and correspondingly lost ability to grow on SC-Ura, consistent with successful linearization (FIG. 3B, top row). The remaining half of cells that were sensitive to Foa was able to grow on SC-Ura, suggesting the synIXR BAC had not been linearized. When comparing cells harboring circular or linear synIXR molecules, there were no apparent changes to colony size or shape, suggesting the linearized construct was mitotically stable. Importantly, in cells lacking the I-SceI recognition site (−I-SceI), the Foa$^R$ phenotype was not observed, demonstrating that linearization depends on this sequence (FIG. 3B, bottom row). Taken together, this work suggests that the telomerator efficient linearizes circular DNA molecules in vivo upon induction.

Example 4: Circular Permutation of a Synthetic Eukaryotic Chromosome

Figure 4:
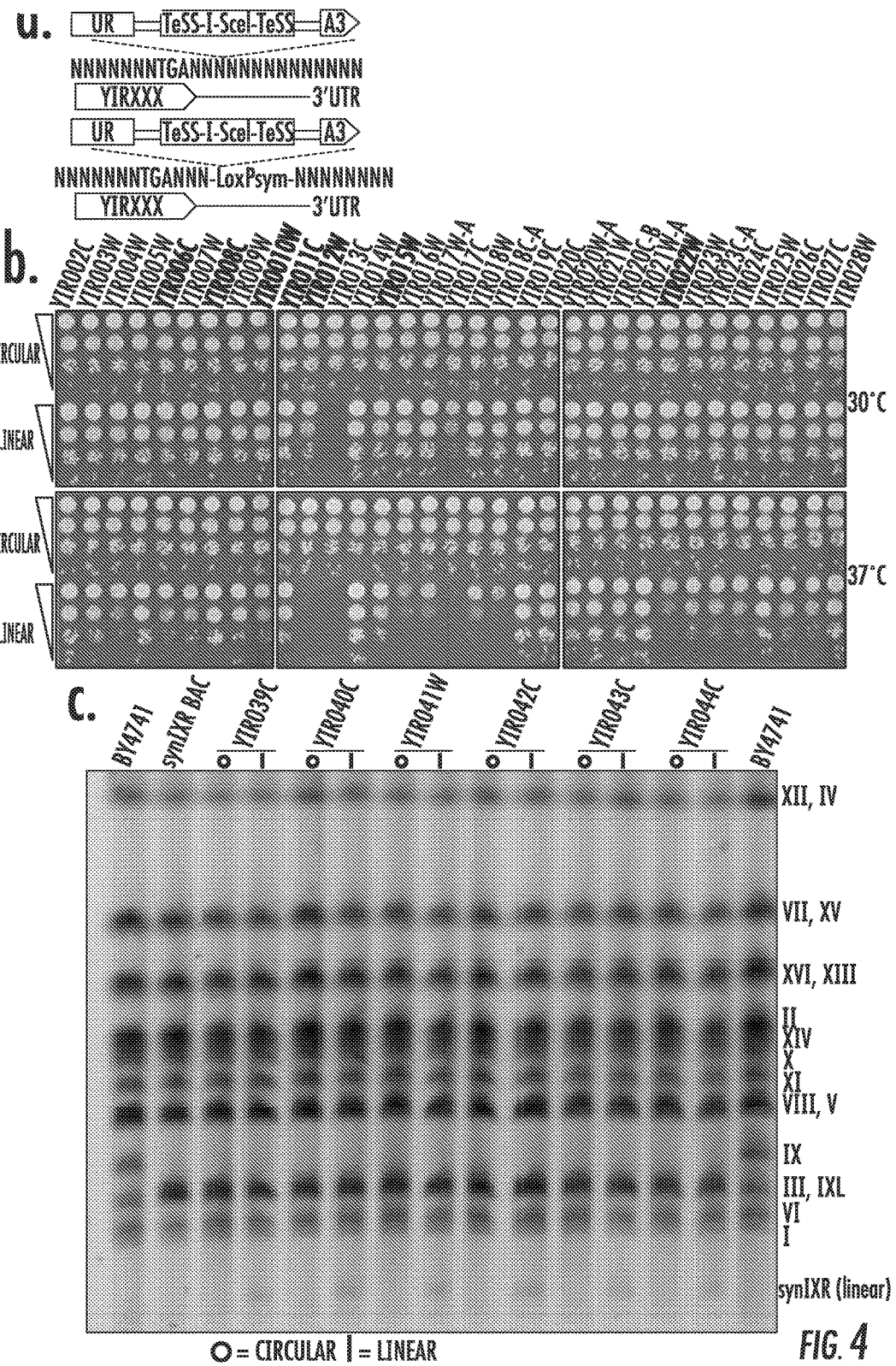
FIG. 4: Circular permutation of a synthetic eukaryotic chromosome, synIXR BAC. (A) Strategy to integrate the telomerator cassette downstream of 54 genes on synIXR BAC. (B) Characterization of permuted strains. The telomerator cassette was integrated downstream of each indicated gene, and growth of strains, pre-(circular) and post-linearization (linear), was assessed at 30° C. (top) or 37° C. (bottom) on rich medium. Shown here are 10-fold serial dilutions after two days growth. Permuted strains not pictured here did not exhibit growth defects. (C) Pulsed field gel showing appearance of linear synIXR after galactose induction in six representative strains (the telomerator was integrated downstream of YIR039C, YIR040C, YIR041W, YIR042C, YIR043C, YIR044C), as compared to a wild type strains encoding a native chromosome IX (BY4741), or the parental strain used for telomerator integrations (synIXR BAC). The circular form of synIXR BAC is not detectable on pulsed field gel. O=circular; I=linear.

The telomerator enables fine control over the location at which a circular DNA molecule is linearized and thus represents a tool to probe the function of gene order, orientation, and chromosomal structure in vivo. For instance, if integrated between two genes, telomerator-driven linearization will yield novel telomere-promixal gene positioning that could lead to subtelomeric silencing. Furthermore, depending on the orientation of each gene with respect to the telomerator cassette, linearization could disrupt either 5' or 3' regulatory elements that drive their transcription. To test these ideas, we integrated the telomerator cassette three base pairs downstream of all 54 chromosome IX genes on synIXR BAC, generating an array of 54 permutable strains. We chose this position as it was previously shown to tolerate the insertion of synthetic sequences (8); indeed synIXR BAC encodes a 34 base pair site-specific recombination site (loxPsym) at this position downstream of every non-essential gene on the BAC with no effect on cell fitness (FIG. 3A). For the telomerator cassette integration, at each of the 47 non-essential genes we "overwrote" the loxPsym site, and for the 7 essential genes that had no pre-exiting loxPsym site we inserted the cassette cleanly 3 base pairs downstream of the stop codon (FIG. 4A). Integration at the correct locus was confirmed for all 54 permutable strains by PCR using a gene-specific primer in combination with a primer that annealed within the telomerator (FIG. 6). We found that at all 54 loci integration of the telomerator caused no noticeable change in fitness (FIG. 4B and data not shown). Notably, the promoter region of the telomerator-encoded URA3 contains a terminator sequence that would polyadenylate incoming transcripts; thus integration of the telomerator 3' to any gene, while disrupting native 3' end forming sequences, provides a built-in, non-native terminator sequence for the resulting transcript. Next, the pGAL-I-SceI construct was transformed into the 54 strains, which were grown in galactose medium for 24 hours to induce linearization. Foa resistant cells were selected, enabling isolation of the permuted array of linearized synIXR-containing strains. To investigate whether the synIXR BACs were linearized, full-length chromosomes from six permuted strains, pre- and post-linearization were chosen and separated by pulse-field gel electrophoresis. Only telomerator-integrated strains subjected to growth in galactose exhibited a band on the gel corresponding to the linearized form of synIXR (FIG. 4C). Of the 54 sites into which the telomerator had been integrated, 53 could be linearized and give rise to viable FoaR colonies. At just one position, YIR013C, linearization of synIXR was lethal (FIG. 4B). YIR013C encodes a non-essential, GATA family zinc finger motif containing protein with no annotated function. While not lethal, many other permuted chromosomes resulted in modest growth defects at 30° C. (FIG. 4B). At 37° C., almost half of all permuted strains grew very slowly. Together, the data indicate that telomerator-induced linearization provides a new way to generate novel phenotypes.

Figure 5:
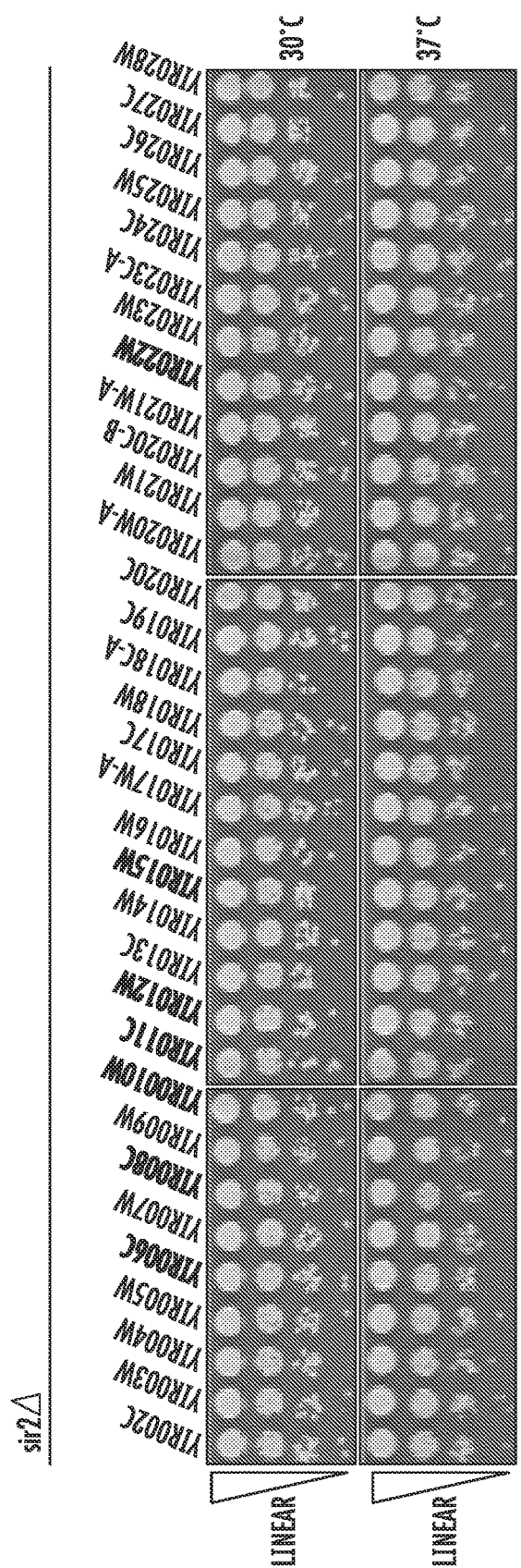
FIG. 5: Deletion of SIR2 rescues growth defects of synIXR BAC circular permutations. The SIR2 gene was deleted in the each of the 54 unique telomerator-containing synIXR BAC strains. Following transformation of the pGAL1-I-SceI construct and growth in galactose, linear permutations were isolated on Foa medium. Shown here are 10-fold serial dilutions after two days growth on rich medium (YPD) at the indicated temperatures. Only the permuted strains corresponding to those pictured in 4b are shown.
Figure 7:
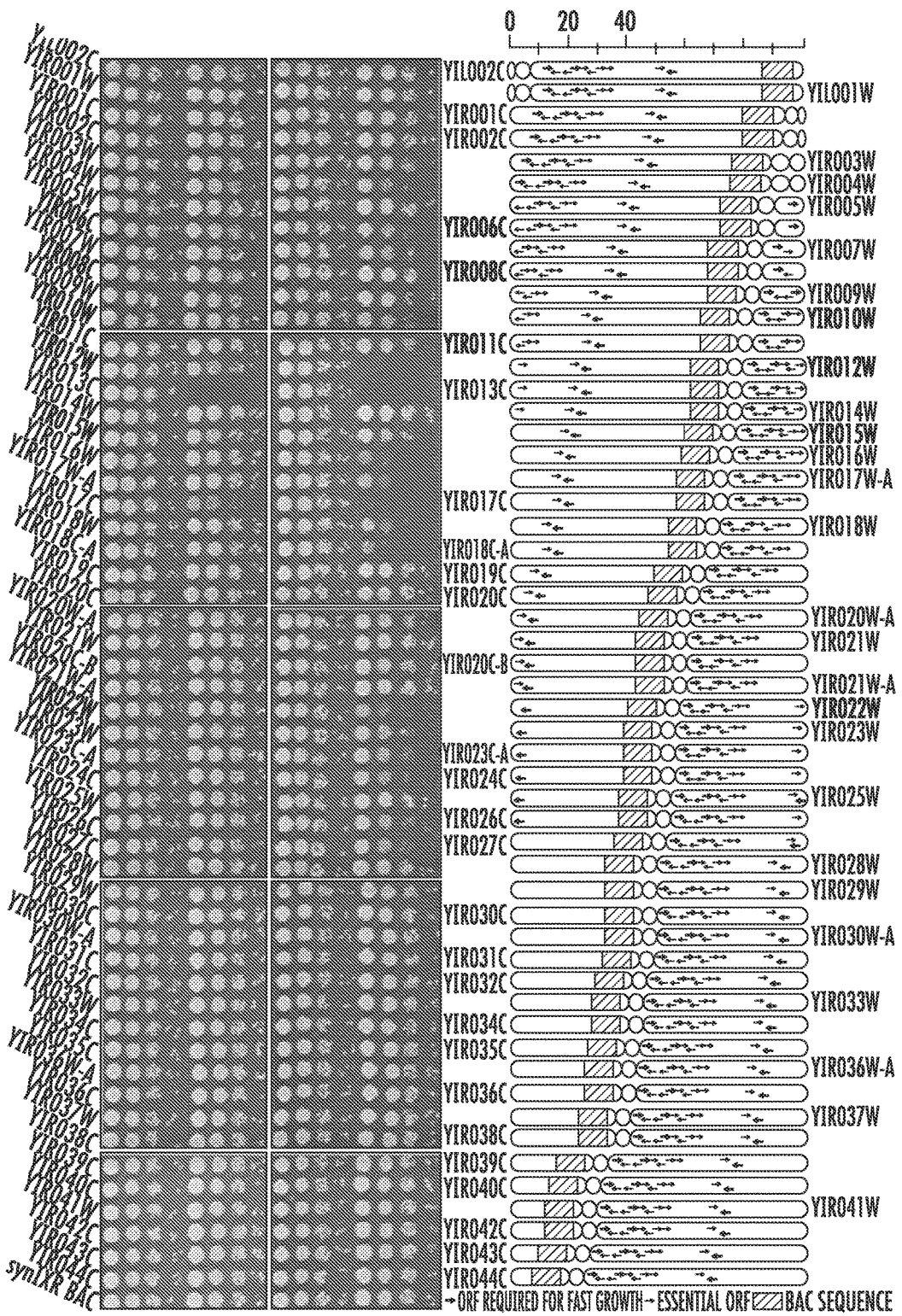
FIG. 7: Position effect of genes expected to impact cell fitness. Left panel: Fitness defects in linearized strains (as in FIG. 3b). Right panel: Orientation and approximate location on linearized synIXR of essential ORFs and ORFs required for fast growth.

Example 5: Telomeric Silencing Mediates Fitness Defects of Linearized synIXR Permutations We hypothesized that telomeric silencing could underlie the fitness defects observed in many of the linear permutations of synIXR (FIG. 3B). Telomeric silencing, or the transcriptional repression of genes in proximity to telomeres, is an epigenetic phenomenon relying on the establishment of heterochromatin that spreads from the ends of chromosomes inwards. Linearization-dependent re-location of essential genes into sub-telomeric regions and the subsequent reduction in expression could have a major impact on impact cell fitness and/or survival. Indeed, mapping the position of the seven essential genes onto the array of linearized permutations of synIXR suggests that fitness defects tend to occur in strains in which one or more essential genes are re-located to within 10 kb of a telomere (FIG. 7). Consequently, they might be subject to silencing, a process mediated in part by the lysine deacetylase enzyme Sir2 (18), which deacetylates histone H4 (19). To test our hypothesis, we deleted SIR2 in each of the 54 linearizable synIXR strains. Following transformation of the pGAL1-I-SceI construct and growth in galactose, cells harboring linearized synIXR molecules were selected on medium containing Foa. We discovered that disruption of telomeric silencing by SIR2 deletion rescued nearly all growth defects associated linear permutations of synIXR (FIG. 5). Notably, this included the location at which we previously could not detect linearization, YIR013C (FIG. 3B) Importantly, these results are consistent with the conclusion that the telomerator-encoded 40 bp telomere seed sequences indeed generate functional telomeres complete with the appropriate establishment of heterochromatin. Moreover, the telomerator clearly provides a new means to probe epigenetic regulation and chromatin architecture as we show that proper gene expression can depend on the chromosomal location/environment in which a gene is positioned.

Example 6: Another Telomerator Sequence

Another approach to introduce the Telomerator sequence into a circular DNA molecule for linearization is to include the TeSS-I-SceI-TeSS sequence as part of the protein coding sequence of the selectable marker. In such embodiments, the TeSS-I-SceI-TeSS sequence is "in-frame" with the selectable marker sequence (i.e., a multiple of 3) such that the resulting protein translation would not be truncated. The TeSS-I-SceI-Tess sequence is inserted into the selectable marker in a position that would not disrupt function of the resulting protein product.

SEQ ID NO:9 shows the TeSS-ISceI-TeSS sequence encoded within the native URA3 coding sequence:

```
                                          (SEQ ID NO: 9)
atgTGTGTGGTGTGTGGGTGTGTGGGTGTGGGTGTGTGGGTAGGG

ATAACAGGGTAATCACCCACCACACACACCCACACACACCACACACCCA

CCCAtcgaaagctacatataaggaacgtgctgctactcatcctagtcct gttgctgccaagctatttaatatcatgcacgaaaagcaaacaaacttgt
```

-continued
```
gtgcttcattggatgttcgtaccaccaaggaattactggagttagttga agcattaggtcccaaaatttgtttactaaaaacacatgtggatatcttg actgattttccatggagggcacagttaagccgctaaaggcattatccg ccaagtacaattttttactcttcgaagacagaaaatttgctgacattgg taatacagtcaaattgcagtactctgcgggtgtatacagaatagcagaa tgggcagacattacgaatgcacacggtgtggtgggcccaggtattgtta gcggtttgaagcaggcggcagaagaagtaacaaaggaacctagaggcct tttgatgttagcagaattgtcatgcaagggctccctatctactggagaa tatactaagggtactgttgacattgcgaagagcgacaaagattttgtta tcggctttattgctcaaagagacatgggtggaagagatgaaggttacga ttggttgattatgacacccggtgtgggtttagatgacaagggagaTgca ttgggtcaacagtatagaaccgtggatgatgtggtGtctacaggatctg acattattattgttggaagaggactatttgcaaagggaagggatgctaa ggtagagggtgaacgttacagaaaagcaggctgggaagcatatttgaga agatgcggccagcaaaactaa
```

The TeSS-ISceI-TeSS sequence, which is 99 bp and thus should be in-frame, is inserted just past the start codon (ATG) of URA3. The lower case letters are native URA3 coding sequence and the upper case letters correspond to the TeSS-ISceI-TeSS A construct encoding SEQ ID NO:9 was built and transformed into yeast. Plasmids were recovered from colonies that grew on SC-Ura plates and sequenced. Clone 1 has the following sequence:

```
                                         (SEQ ID NO: 10)
atgTGTGTGGTGTGTGGGTGTGTGGGTGTGTGGGTGTGTGTGGGTG

TGTGGGTGTGTGGGTAGGGATAACAGGGTAATCACCCACCACACACAC

CCACACACACCACACACCCACCCAtcgaaagctacatataaggaacgt gctgctactcatcctagtcctgttgctgccaagctatttaatatcatg cacgaaaagcaaacaaacttgtgtgatcattggatgttcgtaccacca aggaattactggagttagttgaagcattaggtcccaaaatttgtttac taaaaacacatgtggatatcttgactgattttccatggagggcacag ttaagccgctaaaggcattatccgccaagtacaattttttactcttcg aagacagaaatttgctgacattggtaatacagtcaaattgcagtact ctgcgggtgtatacagaatagcagaatgngcagacattacgaatgcac acggtgtggtgggcccaggtattgttagcggtttgaagcaggcggcag aagaagtaacaaaggaacctagaggcctttgatgttagcagaattgt catgcaagggctccctatctactggagaatatactaagggtactgttg acattgcgaagagcgacaaagattttgttatcggctttattgctcaaa gagacatgggtggaagagatgaaggttacgattggttgattatgacac ccggtgtgggtttagatgacaagggagacgcattgggtcaacagtata gaaccgtggatgatgtggtctctacaggatctgacattattattgttg
```

Clone 2 has the following sequence:

(SEQ ID NO: 11)
atgTGTGTGGTGTGTGGGTGTGTGGGTGTGTGGGTGTGTGGGTAGGGA
TAACAGGGTAATCACCCACCCAtcgaaagctacatataaggaacgtgctg
ctactcatcctagtcctgttgctgccaagctatttaatatcatgcacgaa
aagcaaacaaacttgtgtgatcattggatgttcgtaccaccaaggaatta
ctggagttagttgaagcattaggtcccaaaatttgtttactaaaaacaca
tgtggatatcttgactgattttccatggagggcacagttaagccgctaa
aggcattatccgccaagtacaattttttactatcgaagacagaaaatttg
ctgacattggtaatacagtcaaattgcagtactctgcgggtgtatacaga
atagcagaatgggcagacattacgaatgcacacggtgtggtgggcccagg
tattgttagcggtttgaagcaggcggcagaagaagtaacaaaggaaccta
gaggccttttgatgttagcagaattgtcatgcaagggctccctatctact
ggagaatatactaagggtactgttgacattgcgaagagcgacaaagattt
tgttatcggattattgctcaaagagacatgggtggaagagatgaaggtta
cgattggttgattatgacacccggtgtgggtttagatgacaagggagacg
cattgggtcaacagtatagaaccgtggatgatgtggtctctacaggatct
gacattattattgttggaagaggactatttgcaaagggaagggatgctaa
ggtagagggtgaacgttacagaaaagcaggctgggaagcatatttgagaa
gatgcggccagcaaaactaa Clone 3 has the following sequence:

(SEQ ID NO: 12)
atgTGTGTGGTGTGTGGGTGTGTGGGTGTGTGGGTGTGTGGGTAGGG
ATAACAGGGTAATCACCCACCACACACACCCACACACACCACACACCCA
CCCAtcgaaagctacatataaggaacgtgctgctactcatcctagtcct
gttgctgccaagctatttaatatcatgcacgaaaagcaaacaaacttgt
gtgcttcattggatgttcgtaccaccaaggaattactggagttagttga
agcattaggtcccaaaatttgtttactaaaaacacatgtggatatcttg
actgattttccatggagggcacagttaagccgctaaaggcattatccg
ccaagtacaattttttactcttcgaagacagaaaatttgctgacattgg
taatacagtcaaattgcagtactctgcgggtgtatacagaatagcagaa
tgggcagacattacgaatgcacacggtgtggtgggcccaggtattgtta
gcggtttgaagcangcggcagaagaagtaacaaaggaacctagaggcct
tttgatgttagcagaattgtcatgcaagggctccctatctactggagaa
tatactaagggtactgttgacattgcgaagagcgacaaagattttgtta
tcggctttattgctcaaagagacatgggtggaagagatgaaggttacga
ttggttgattatgacacccggtgtgggtttagatgacaagggagacgca ttgggtcaacagtatagaaccgtggatgatgtggtctctacaggatctg
acattattattgttggaagaggactatttgcaaagggaagggatgctaa
ggtagagggtgaacgttacagaaaagcaggctgggaagcatatttgaga
agatgcggccagcaaaactaa Clone 4 has the following sequence:

(SEQ ID NO: 13)
atgTGTGTGGTGTGTGGGTGTGTGTGGGTGTGTGGGTGTGTGGGTAGGG
ATAACAGGGTAATCACCCACCCAtcgaaagctacatataaggaacgtgc
tgctactcatcctagtcctgttgctgccaagctatttaatatcatgcac
gaaaagcaaacaaacttgtgtgatcattggatgttcgtaccaccaagga
attactggagttagttgaagcattaggtcccaaaatttgtttactaaaa
acacatgtggatatcttgactgattttccatggagggcacagttaagc
cgctaaaggcattatccgccaagtacaattttttactcttcgaagacag
aaaatttgctgacattggtaatacagtcaaattgcagtactctgcgggt
gtatacagaatagcagaatgggcagacattacgaatgcacacggtgtgg
tgggcccaggtattgttagcggtttgaagcaggcggcagaagaagtaac
aaaggaacctagaggccttttgatgttagcagaattgtcatgcaagggc
tccctatctactggngaatatactaagggtactgttgacattgcgaaga
gcgacaaagattttgttatcggctttattgctcaaagagacatgggtgg
aagagatgaaggttacgattggttgattatgacacccggtgtgggttta
gatgacaagggagacgcattgggtcaacagtatagaaccgtggatgatg
tggtctctacaggatctgacattattattgttggaagaggactatttgc
aaagggaagggatgctaaggtagagggtgaacgttacagaaaagcaggc
tgggaagcatatttgagaagatgcggccagcaaaactaa The TeSS repeats are unstable in the absence of selection (i.e., growth on SC-Ura), likely due to slippage during DNA replication. Clone 3 matches exactly the designed sequence, suggesting this design can indeed complement growth. Two out of four clones have a truncated CA repeat, which likely increases the stability. Other embodiments of the telomerator can incorporate this design to generate a more stable construct.

REFERENCES

1. A. Goffeau et al., *Science* 274, 546 (Oct. 25, 1996).
2. L. Clarke, J. Carbon, *Nature* 287, 504 (Oct. 9, 1980).
3. J. Shampay, J. W. Szostak, E. H. Blackburn, *Nature* 310, 154 (Jul. 12-18, 1984).
4. R. W. Walmsley, C. S. Chan, B. K. Tye, T. D. Petes, *Nature* 310, 157 (Jul. 12-18, 1984).
5. Y. Ueda et al., *J Biosci Bioeng* 113, 675 (June, 2012).
6. K. Murakami et al., *Appl Microbiol Biotechnol* 75, 589 (June, 2007).
7. R. J. Reid et al., *Genetics* 180, 1799 (December, 2008).
8. J. S. Dymond et al., *Nature* 477, 471 (Sep. 22, 2011).
9. A. Plessis, A. Perrin, J. E. Haber, B. Dujon, *Genetics* 130, 451 (March, 1992).
10. L. Colleaux, L. D'Auriol, F. Galibert, B. Dujon, *Proc Natl Acad Sci USA* 85, 6022 (August, 1988).
11. A. P. Davis, L. S. Symington, *Mol Cell Biol* 24, 2344 (March, 2004).

12. X. Yu, A. Gabriel, *Mol Cell* 4, 873 (November, 1999).
13. J. D. Boeke, J. Trueheart, G. Natsoulis, G. R. Fink, *Methods Enzymol* 154, 164 (1987).
14. R. S. Sikorski, P. Hieter, *Genetics* 122, 19 (May, 1989).
15. C. B. Brachmann et al., *Yeast* 14, 115 (Jan. 30, 1998).
16. R. T. Surosky, C. S. Newlon, B. K. Tye, *Proc Natl Acad Sci USA* 83, 414 (January, 1986).
17. W. J. Blake et al., *Nucleic Acids Res* 38, 2594 (May, 2010).
18. O. M. Aparicio, B. L. Billington, D. E. Gottschling, *Cell* 66, 1279 (Sep. 20, 1991).
19. S. Imai, C. M. Armstrong, M. Kaeberlein, L. Guarente, *Nature* 403, 795 (Feb. 17, 2000).
20. G. M. Dani, V. A. Zakian, *Proc Natl Acad Sci USA* 80, 3406 (June, 1983).
21. A. W. Murray, J. W. Szostak, *Nature* 305, 189 (Sep. 15-21, 1983).
22. J. E. Haber, P. C. Thorburn, D. Rogers, *Genetics* 106, 185 (February, 1984).
23. A. W. Murray, J. W. Szostak, *Mol Cell Biol* 6, 3166 (September, 1986).
24. Y. Kazuki et al., *Gene Ther* 18, 384 (April, 2011).
25. R. Saffery et al., *Proc Natl Acad Sci USA* 98, 5705 (May 8, 2001).
26. J. J. Harrington, G. Van Bokkelen, R. W. Mays, K. Gustashaw, H. F. Willard, *Nat Genet* 15, 345 (April, 1997).
27. T. A. Ebersole et al., *Hum Mol Genet* 9, 1623 (Jul. 1, 2000).
28. M. Ikeno et al., *Nat Biotechnol* 16, 431 (May, 1998).
29. D. Moralli, P. Vagnarelli, M. Bensi, L. De Carli, E. Raimondi, *Cytogenet Cell Genet* 94, 113 (2001).
30. Y. Iida et al., *DNA Res* 17, 293 (October, 2010).
31. A. J. Noel, W. Wende, A. Pingoud, *J Biol Chem* 279, 6794 (Feb. 20, 2004).
32. D. G. Gibson et al., *Nat Methods* 6, 343 (May, 2009).
33. M. Lisby, U. H. Mortensen, R. Rothstein, *Nat Cell Biol* 5, 572 (June, 2003).
34. D. C. Schwartz, C. R. Cantor, *Cell* 37, 67 (May, 1984).
35. E. A. Winzeler et al., *Science* 285, 901 (Aug. 6, 1999).

We claim:

1. A telomerator cassette comprising a nucleic acid encoding a selectable marker, wherein the nucleic acid encoding a selectable marker is interrupted by an intron comprising an endonuclease recognition site flanked by telomere seed sequences.

2. The telomerator cassette of claim 1, wherein the intron is the ACT1 intron.

3. The telomerator cassette of claim 1, wherein the selectable marker is an auxotrophic marker.

4. The telomerator cassette of claim 3, wherein the auxotrophic marker is the URA3 gene.

5. The telomerator cassette of claim 1, wherein the endonuclease recognition site is specific for I-SceI.

6. The telomerator cassette of claim 5, wherein the I-SceI endonuclease recognition site comprises SEQ ID NO:2.

7. The telomerator cassette of claim 1, wherein the telomere seed sequences comprise SEQ ID NO:1 and SEQ ID NO:3.

8. A circular chromosome comprising the telomerator cassette of claim 1.

9. A eukaryotic host cell comprising the circular chromosome of claim 8.

10. The eukaryotic host cell of claim 9, wherein the eukaryote is yeast.

11. The eukaryotic host cell of claim 10, wherein the yeast is *S. cerevisiae*.

12. The eukaryotic host cell of claim 9, wherein the host cell comprises a vector encoding the endonuclease under the control of an inducible promoter.

13. A telomerator cassette comprising a nucleic acid that encodes the auxotrophic marker URA3, wherein the nucleic acid is interrupted by an intron that comprises the I-SceI endonuclease recognition site flanked by telomere seed sequences.

14. The telomerator cassette of claim 13, wherein the telomere seed sequences comprise SEQ ID NO:1 and SEQ ID NO:3.

15. The telomerator cassette of claim 13, wherein the I-SceI endonuclease recognition site comprises SEQ ID NO:2.

16. A circular chromosome comprising the telomerator cassette of claim 13.

17. A yeast host cell comprising the circular chromosome of claim 16.

18. The yeast host cell of claim 17, wherein the yeast host cell comprises a vector encoding the I-SceI endonuclease under the control of an inducible promoter.

19. The yeast host cell of claim 18, wherein the inducible promoter is the GAL1 promoter.

20. A yeast host cell comprising:
    a. a circular chromosome comprising a telomerator cassette encoding a selectable marker, wherein the nucleic acid encoding the selectable marker is interrupted by an intron that comprises an endonuclease recognition site flanked by telomere seed sequences; and
    b. a vector encoding the endonuclease under the control of an inducible promoter.

21. The yeast host cell of claim 20, wherein the selectable marker is an auxotrophic marker.

22. The yeast host cell of claim 21, wherein the auxotrophic marker is the URA3 gene.

23. The yeast host cell of claim 20, wherein the endonuclease recognition site is specific for I-SceI.

24. The yeast host cell of claim 23, wherein the I-SceI endonuclease recognition site comprises SEQ ID NO:2.

25. The yeast host cell of claim 20, wherein the telomere seed sequences comprise SEQ ID NO:1 and SEQ ID NO:3.

26. A method for engineering a circular chromosome capable of being inducibly linearized comprising the step of integrating a telomerator cassette into a circular chromosome, wherein the telomerator cassette comprises a nucleic acid encoding a selectable marker, wherein the nucleic acid encoding a selectable marker is interrupted by an intron comprising an endonuclease recognition site flanked by telomere seed sequences.

27. The method of claim 26, wherein the integrating step is accomplished by transforming a telomerator cassette into a host cell comprising the circular chromosome.

28. The method of claim 27, wherein the host cell comprises a vector encoding the endonuclease under the control of an inducible promoter.

29. A telomerator cassette comprising a nucleic acid encoding a selectable marker, wherein the nucleic acid encoding the selectable marker is interrupted by an endonuclease recognition site flanked by telomere seed sequences such that the selectable marker retains its function.

30. The telomerator cassette of claim 29, wherein the selectable marker is an auxotrophic marker.

31. The telomerator cassette of claim 30, wherein the auxotrophic marker is the URA3 gene.

32. The telomerator cassette of claim 29, wherein the endonuclease recognition site is specific for I-SceI.

33. The telomerator cassette of claim 32, wherein the I-SceI endonuclease recognition site comprises SEQ ID NO:2.

34. The telomerator cassette of claim 29, wherein the telomere seed sequences comprise SEQ ID NO:1 and SEQ ID NO:3.

35. A circular chromosome comprising the telomerator cassette of claim 29.

36. A eukaryotic host cell comprising the circular chromosome of claim 35.

* * * * *